US009488655B2

(12) United States Patent
Farias-Eisner et al.

(10) Patent No.: US 9,488,655 B2
(45) Date of Patent: Nov. 8, 2016

(54) BIOMARKERS FOR DETECTION OF EARLY- AND LATE-STAGE ENDOMETRIAL CANCER

(75) Inventors: Robin Farias-Eisner, Calabasas, CA (US); Srinivasa T. Reddy, Cerritos, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 250 days.

(21) Appl. No.: 12/860,293

(22) Filed: Aug. 20, 2010

(65) Prior Publication Data

US 2011/0027894 A1 Feb. 3, 2011

Related U.S. Application Data

(60) Continuation-in-part of application No. 12/630,458, filed on Dec. 3, 2009, now Pat. No. 8,323,915, which is a division of application No. 11/571,986, filed as application No. PCT/US2005/024985 on Jul. 14, 2005, now Pat. No. 7,670,792.

(60) Provisional application No. 60/674,489, filed on Apr. 25, 2005, provisional application No. 60/588,007, filed on Jul. 14, 2004.

(51) Int. Cl.
*G01N 33/574* (2006.01)

(52) U.S. Cl.
CPC ... *G01N 33/57442* (2013.01); *G01N 2333/775* (2013.01); *G01N 2333/79* (2013.01)

(58) Field of Classification Search
None
See application file for complete search history.

(56) References Cited

U.S. PATENT DOCUMENTS

| | | | |
|---|---|---|---|
| 5,114,863 A | 5/1992 | McCombs et al. |
| 5,891,641 A | 4/1999 | Prusiner et al. |
| 5,955,582 A | 9/1999 | Newman et al. |
| 7,191,068 B2 | 3/2007 | Rosenfeld et al. |
| 7,291,461 B2 | 11/2007 | Welch et al. |
| 7,510,842 B2 | 3/2009 | Podust et al. |
| 7,510,881 B2 | 3/2009 | Ramael et al. |
| 7,575,876 B2 | 8/2009 | Zhang et al. |
| 7,589,174 B2 | 9/2009 | Argon et al. |
| 7,604,948 B2 | 10/2009 | Amaral et al. |
| 7,670,792 B2 | 3/2010 | Farias-Eisner et al. |
| 2003/0027216 A1 | 2/2003 | Kiernan et al. |
| 2005/0059013 A1 | 3/2005 | Chan et al. |
| 2006/0068405 A1 | 3/2006 | Diber et al. |
| 2006/0094039 A1 | 5/2006 | Rosenfeld et al. |
| 2006/0257866 A1 | 11/2006 | Welch et al. |
| 2010/0081151 A1 | 4/2010 | Farias-Eisner et al. |

FOREIGN PATENT DOCUMENTS

| | | |
|---|---|---|
| EP | 0 201 187 | 11/1986 |
| WO | WO91/08488 | 6/1991 |
| WO | WO2004/012588 | 2/2004 |
| WO | WO2004/013609 | 2/2004 |
| WO | WO2005/093413 | 10/2005 |
| WO | WO 2006/099126 | 9/2006 |
| WO | WO2006099126 | * 9/2006 |

OTHER PUBLICATIONS

Faria-Eisner et al, Amer J Obs and Gyn Jan. 2010.*
Extended European Search Report dated Sep. 5, 2011 cited in corresponding EP Application No. 10009544.7, 10 pp.
Kozak, Katherine R., "Characterization of serum biomarkers for detection of early stage ovarian cancer", Proteomics, 2005, 5: 4589-4596.
Kozak, Katherine R., "Identification of biomarkers for ovarian cancer . . . prognosis", PNAS, Oct. 14, 2003, 100(21): 12343-12348.
Munstedt, Karsten, "Impact of hemoglobin levels before and during chemotherapy . . . cancer",, Int'l Journal of Oncology, 2003, 23(3): 837-843.
Obermair, Andreas, "The relationship of pretreatment serum hemoglobin level . . . review", 1998, American Cancer Society, XP008056584, 83(4): 726-731.
Rai, Alex J., "Proteomic approaches to tumor marker discovery", Dec. 2002, Arch Pathol Lab Med, 126: 1518-1526.
Tosner, J., "Serum prealbumin, transferrin and alpha-1-acid glycoprotein in patients with gynecological carcinomas", 1988, Neoplasma, Sciences, 35(4):403-412.
Van Belle, S.J.-P, What is the value of hemoglobin as a prognostic and predictive factor in cancer?, 2004, EJC Supplements, XP008056585, 2(2): 11-19.
Zhang, Zhen, "Protein identification and immunoassay evaluation of a panel of biomarkers . . . ovarian cancer", AACR Meeting Abstracts Online, 2004, 45: Abstract #1063.
Extended European Search Report, EP Appliciation No. 10003541. 9-1223, Jul. 28, 2010, 10 pp.
Duk, J.M. et al., "CA 125: A useful marker in endometrial carcinoma", 1986, Amer J. of Obstetrics and Gynecology, 155(5): 1097-1102. 1 page Abstract.
Lo, S.S.T. et al., "Prognostic Significance of Tumour Markers in Endometrial Cancer", 1997, Tumor Biology, 18:241-249.

* cited by examiner

*Primary Examiner* — Lei Yao
(74) *Attorney, Agent, or Firm* — Karen S Canady; canady + lortz LLP

(57) ABSTRACT

Biomarker proteins that can be used in the diagnosis of early-stage endometrial cancer are described. Methods of screening for endometrial cancer, as well as methods of detecting and monitoring the status of endometrial cancer are provided. The biomarkers can be used to detect a variety of endometrial cancers, including endometroid carcinoma, clear cell carcinoma and serous carcinoma.

12 Claims, 9 Drawing Sheets

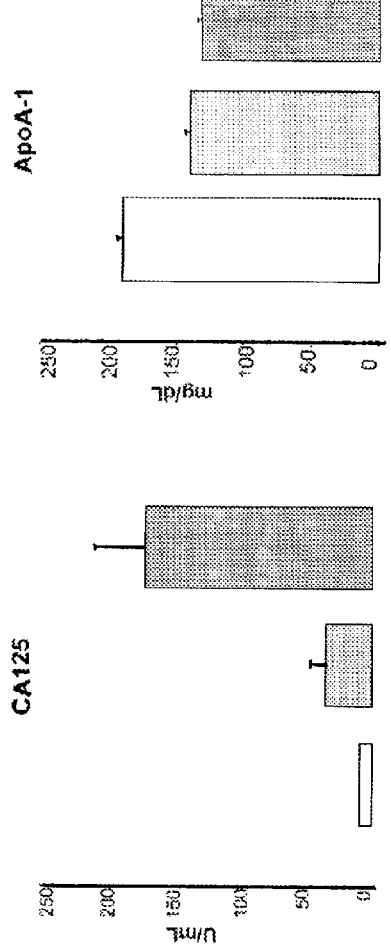
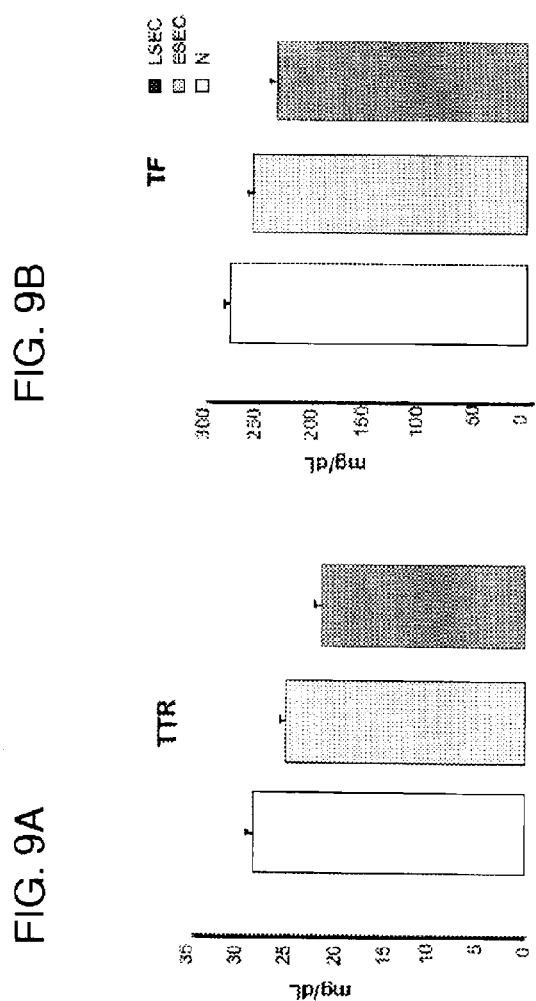
FIG. 9A
FIG. 9B
FIG. 9C
FIG. 9D

BIOMARKERS FOR DETECTION OF EARLY- AND LATE-STAGE ENDOMETRIAL CANCER This application is a continuation-in-part of U.S. patent application Ser. No. 12/630,458, filed Dec. 3, 2009, which is a divisional of U.S. patent application Ser. No. 11/571,986, filed Jul. 18, 2007, now U.S. Pat. No. 7,670,792, which is a filing under 35 U.S.C. §371 of application number PCT/US05/24985, filed Jul. 14, 2005, which claims the benefit of U.S. provisional patent application Nos. 60/674,489, filed Apr. 25, 2005, and 60/588,007, filed Jul. 14, 2004, the entire contents of each of which is incorporated herein by reference.

Throughout this application various publications are referenced. The disclosures of these publications in their entireties are hereby incorporated by reference into this application in order to describe more fully the state of the art to which this invention pertains.

TECHNICAL FIELD OF THE INVENTION

The present invention relates generally to detection and therapy of cancer. The invention is more specifically related to a novel panel of biomarkers and their use in early diagnosis and prognosis of women's cancers, particularly ovarian and endometrial cancers. Antibodies and antisense and/or interference nucleotides and other inhibitory molecules directed against these targets can be used in vaccines and pharmaceutical compositions for the treatment of various cancers expressing the biomarkers identified herein, as well as in methods of detecting and assessing the malignancy of such cancers. The invention further provides methods for identifying molecules useful in the treatment and detection of cancer.

BACKGROUND OF THE INVENTION

Endometrial carcinoma is the most common gynecologic cancer in the United States, with >7400 deaths per year and a death rate that has doubled since 1985. The increase in mortality rates in women with endometrial cancer is related to an increase in patients with advanced-stage cancers and a larger proportion of high-risk histologic conditions. Current diagnostic approaches rely on endometrial sampling of macroscopic disease that is driven by the presence of symptoms and signs that include vaginal bleeding and metrorrhagia. The key to an improved progression-free survival and overall survival is the early diagnosis of microinvasive disease, which is curable more readily with the use of either hormonal or surgical treatment modalities.

To date, there are no reliable serum biomarkers in clinical use for the detection of endometrioid, clear cell, or papillary serous adenocarcinoma of the endometrium. Serum cancer antigen 125 (CA125) is a high molecular weight glycoprotein and serum CA125 levels ≤35 units/mL are accepted as normal. CA125 is currently only relatively accurate in the detection of late stage ovarian cancer (papillary serous histologic subtype), is not used for the detection of endometrial cancer.

Although novel proteomic-based approaches have been used successfully to detect and diagnose a number of different types of cancers, none have been reported for endometrial cancer. We analyzed protein profiles using surface enhanced laser desorption and ionization time-of-flight mass spectroscopy and identified 3 serum proteins (namely, apolipoprotein-1 [ApoA-I], prealbumin [transthyretin or TTR], and transferrin [TF]) for the early detection of ovarian cancer. We have further discovered that the 3 markers that were described for ovarian cancer can be used in the diagnosis of early- or late-stage endometrial cancer. The invention therefore addresses the need for improved tools to permit the early detection and prognosis of cancer, particularly endometrial and ovarian cancers. There also remains a need for targets useful in the detection and treatment of cancer.

SUMMARY OF THE INVENTION

The invention meets these needs and others by providing materials and methods for the treatment and detection of cancer. The present invention identifies multiple biomarker proteins that can be used in the diagnosis of early-stage ovarian cancer and for both early- and late-stage endometrial cancer. The invention provides biomarker panels that permit the distinction of patients with ovarian neoplasia (benign or malignant) from normal subjects, and allow the identification of patients with early-stage (stage I/II) ovarian cancer, distinct from those patients with benign ovarian tumors or normal individuals. In addition, in a blind test, the biomarker panels described herein distinguished diseased from healthy patients. The invention additionally provides a panel of 3 biomarkers, apolipoprotein-1 (ApoA-I), prealbumin (TTR) and transferrin (TF), a subset of the ovarian cancer biomarkers ("OC biomarkers"), that distinguish normal samples from both early-stage and late-stage endometrial cancer.

Cancer can be detected by analyzing a tissue specimen for the presence of an OC biomarker panel of expression. In one embodiment, the invention provides a method of detecting cancer in a specimen from a subject comprising examining the expression profile of at least two OC related molecules in the specimen, wherein the OC related molecules are selected from a first group of OC related molecules that are overexpressed in ovarian neoplasia and a second group of OC related molecules that are underexpressed in ovarian neoplasia. In some embodiments, overexpression of a member of the first group of OC related molecules comprises an increase of at least about two-fold relative to normal tissue, while underexpression of a member of the second group of OC related molecules comprises a decrease of at least about two-fold. In another embodiment, the method for detecting cancer comprises measuring the amount of one or more OC molecules in a tissue sample of the subject. Typically, the method comprises measuring at least three biomarkers in the tissue sample. The method further comprises comparing the measurements of the biomarkers in the tissue sample to a known profile of the biomarkers in normal tissue. This method can be adapted for screening to distinguish patients with ovarian neoplasia from normal patients, as well as to distinguish patients having benign versus malignant neoplasia.

For detection of endometrial cancer, the method comprises examining the expression profiles of 3 biomarkers in a specimen from the subject. The examining can comprise measuring serum levels of the 3 biomarkers, ApoAI, TTR and TF. Reduced serum levels of these 3 biomarkers is indicative of endometrial cancer. In some embodiments, the method further comprises measuring serum levels of CA125. Increased serum levels of CA125 are indicative of endometrial cancer.

The invention provides a method of screening for status of endometrial cancer in a subject, and a method of detecting endometrial cancer in a test subject. The methods can detect early stage endometrial cancer, and also late stage endometrial cancer. The method comprises measuring three biomarkers consisting of transthyretin, apolipoprotein AI (ApoAI) and transferrin in a test sample of the subject, and comparing the measured three biomarkers of the test sample to a measurement of the three biomarkers in a normal sample. A decrease in the measured three biomarkers of the test sample compared to the measurement of the three biomarkers in the normal sample is indicative of endometrial cancer. The method can optionally further comprise measuring CA-125 in a test sample of the subject and comparing the measured CA-125 to a measurement of CA-125 in a normal specimen. An increase in the measured CA-125 of the test sample compared to the normal sample is indicative of endometrial cancer.

In one embodiment, the decrease in the measured three biomarkers that is indicative of cancer is a decrease of at least 5% compared to the normal sample. In another embodiment, the decrease is at least 10% compared to the normal sample. In yet another embodiment, the decrease is at least 20% compared to the normal sample.

Also provided is a method of monitoring status of endometrial cancer in a test subject. The method comprises measuring biomarkers consisting of TTR, ApoAI and TF in a first test sample obtained from the test subject at a first time point; measuring biomarkers consisting of TTR, ApoAI and TF in a second test sample obtained from the test subject at a second time point; and comparing the amount of the biomarkers in the second test sample with the amount of biomarkers observed in the first test sample. Increased TTR, ApoAI and TF in the second test sample, relative to the first test sample, is indicative of reduced endometrial cancer in the test subject.

In a typical embodiment, the sample or specimen comprises serum. The sample can comprise serum, blood, plasma, or other suitable tissue specimen. The measuring can comprise immunoassay, spectrometry, or other conventional assay for such biomarkers. In one embodiment, the spectrometry comprises surface enhanced laser desorption/ionization (SELDI) mass spectrometry. A typical immunoassay would be an enzyme immunoassay, such as ELISA.

The invention further provides a kit. The kit comprises one or more agents that bind ApoAI, TTR and TF, and optionally, instructions for use of the agents for determining status of endometrial cancer. The kit can further comprise a container for housing the at least one agent. In some embodiments, the kit further comprises an agent that binds CA125. The agents can optionally be labeled with a detectable marker.

In another embodiment, the kit comprises at least one agent that binds a biomarker selected from α-hemoglobin, β-hemoglobin, alpha1-antitrypsin (α1-AT) and any combination thereof; and instructions for use of the at least one agent for determining status of ovarian neoplasia in a test sample. The kit can also comprise at least one agent that binds a biomarker selected from transthyretin, ApoAI, transferrin, CA125 and any combination thereof.

In some embodiments, the kit further comprises a substrate to which the at least one agent is bound. The agent can be an antibody that specifically binds the biomarker, and/or a mass spectrometry probe. The status of neoplasia to be detected by the kit can comprise: absence of neoplasia, benign, low malignant potential (LMP) or malignant neoplasia.

The methods provided by the invention include a method for inhibiting proliferation of cancer cells comprising contacting a cancer cell with a molecule that disrupts the biological activity of an OC molecule. Typically, the biological activity comprises specific binding of OC to an OC antibody or expression of an OC polynucleotide. Other methods provided include a method for treating cancer in a subject by administering to the subject a molecule that disrupts the biological activity of an OC molecule, a method for detecting cancer, and a method for identifying a cancer that is malignant.

In addition, the invention provides endometrial and/or ovarian cancer (OC) related molecules, compositions and additional kits comprising OC related molecules, and methods of using OC related molecules for the treatment and detection of cancer. In one embodiment, the invention provides an expression vector comprising a nucleic acid molecule that encodes an OC protein operably linked to an expression control sequence. The nucleic acid molecule may encode the OC protein in a sense or anti-sense orientation, depending on the intended use. Also provided are host cells containing such expression vectors, which can be used for the production of OC related molecules. In some embodiments, the nucleic acid molecule is labeled with a detectable marker, or provided in a composition with a pharmaceutically acceptable carrier.

The invention additionally provides OC polypeptides, including immunogenic OC peptides. The OC polypeptide may be provided in a variety of forms, as appropriate for a particular use, including, for example, in a soluble form, immobilized on a substrate, or in combination with a pharmaceutically acceptable carrier. Antibodies directed against such OC polypeptides are also provided. In some embodiments, the antibody is labeled with a detectable marker, or provided in a composition with a pharmaceutically acceptable carrier.

BRIEF DESCRIPTION OF THE FIGURES

FIGS. 9A-9D show serum levels of four markers (CA125, ApoA-I, TTR and TF), plotted as mean with standard error. Use of the Student t test showed that expression for each protein in patient samples significantly differed from normal samples (all probability values were <0.01).

DETAILED DESCRIPTION OF THE INVENTION

The present invention is based on the discovery of biomarker proteins that can be used in the diagnosis of early-stage endometrial and/or ovarian cancer. Three biomarkers, ApoA-I, TTR and TF, can detect early-stage disease, when hormonal or surgical treatment modalities can be used to cure disease and before the presence of clinical symptoms or signs. The ovarian biomarkers not only permit the distinction of patients with ovarian neoplasia (benign or malignant) from normal subjects, but they also allow the identification and distinction of patients with early-stage (stage I/II) ovarian cancer from those patients with benign ovarian tumors or normal individuals.

DEFINITIONS

All scientific and technical terms used in this application have meanings commonly used in the art unless otherwise specified. As used in this application, the following words or phrases have the meanings specified.

As used herein, "OC" refers to ovarian cancer and "EC" refers to endometrial cancer.

As used herein, "OC related molecule" or "OC biomarker" refers to any one, alone or in combination with other, of the novel biomarkers or a novel panel of biomarkers identified herein as associated with ovarian cancer. A biomarker is associated with ovarian cancer if its level (amount of molecule present) is up-regulated or down-regulated in neoplastic versus normal tissue or in malignant versus non-malignant tissue. "OC related molecule" includes OC polypeptides, polynucleotides encoding OC polypeptides, polynucleotides complementary to those encoding OC polypeptides, antibodies that specifically recognize and bind OC polypeptides. Three of the OC biomarkers identified herein (ApoA-I, TTR and TR) are also identified herein as EC biomarkers.

Figure 1:
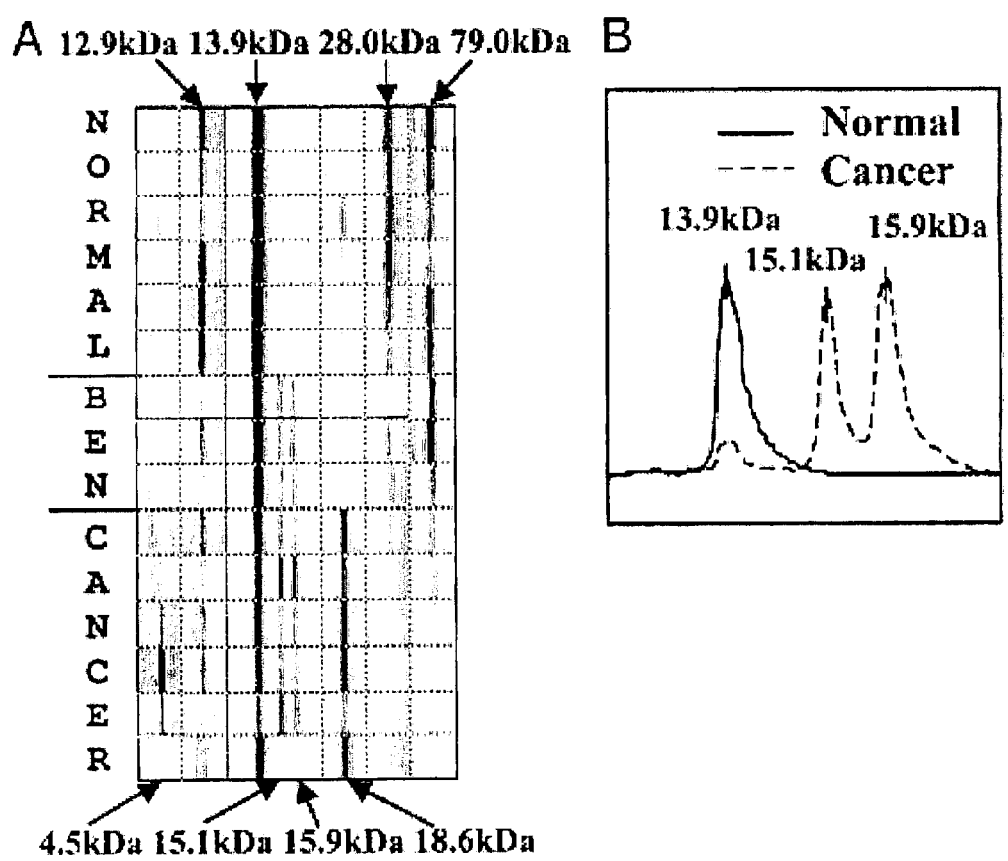
FIGS. 1A-1B show differentially expressed ovarian cancer-associated serum proteins. (1A) Detection of differentially expressed ovarian cancer-associated serum proteins. A representative pseudogel view of SELDI-TOF-MS analysis of serum samples, processed on a SAX2 chip surface, shows relative abundance of potential ovarian cancer markers. The six spectral protein profiles at the top represent serum from healthy individuals, three benign samples are represented in the middle section, and the six spectral profiles on the bottom represent serum from patients with ovarian cancer. (1B) Representative spectral overlay of serum from a healthy (solid line) vs. diseased (dashed line) individual. The overlay shows that there is a decrease of protein 13.9 kDa in serum from ovarian cancer patients, whereas concurrently there is an increase of the proteins 15.1 kDa and 15.9 kDa. Numbers in the mass spectra represent the observed mass of the marker in that particular sample.
Figure 7:
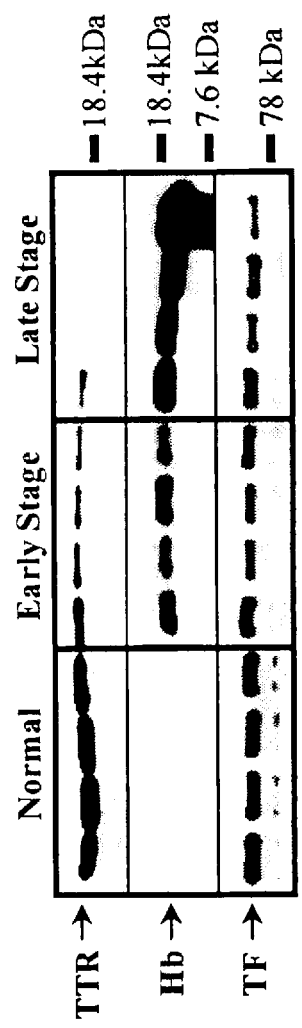
FIG. 7 shows that TTR, Hb, and TF are differentially expressed in serum from ovarian cancer patients as determined by Western analysis. Total serum protein was determined by Bradford assay (Sigma-Aldrich, St. Louis Mo.) using BSA standards and equal protein concentrations were loaded onto SDS-PAGE for TTR, Hb and TF. For the TTR Western, 1 μg total serum protein was resolved on a 15% gel. TTR primary antibody was used at a 1:1000 dilution and the secondary anti-rabbit HRP at 1:4,000. For the Hb Western, 30 μg total serum protein was resolved on a 15% gel. Hb primary antibody was used at a 1:1,000 dilution and the secondary anti-goat HRP at 1:4,000. For the TF Western, 0.1 μg total serum protein was resolved on a 4-15% gradient gel. TF primary antibody was used at a 1:2,000 dilution and secondary anti-rabbit HRP at 1:4,000. Molecular weight protein markers correlating to each gel are indicated.

As used herein, "OC biomarker pattern of expression" refers to a pattern of protein expression substantially similar to that shown in FIG. 1 herein as "CANCER"; or the pattern shown in FIG. 7 as "Early Stage" or "Late Stage". This pattern of expression can be detected by any of the methods described herein.

As used herein, "biological activity of OC" refers to the specific binding of OC to an OC binding partner, such as an OC receptor or antibody, to the expression of an OC polynucleotide, and to the growth regulatory effects of OC related molecules.

As used herein, "specimen" and "sample" are used interchangeably to refer to serum, blood, plasma, vaginal secretions, urine, saliva, tears, a tumor specimen, or other suitable specimen obtained from a test or normal subject.

As used here, "m/z" or "m/z ratio" refers to mass-to-charge ratio, as determined by the SELDI-mass spectroscopy protocol described in U.S. patent publication number 2005/0059013 (Mar. 17, 2005). The masses for the biomarkers described herein are considered accurate to within 0.15 percent of the specified value. Assigned m/z ratios are based on the identification of peaks in the spectrum that represent the signal generated by an analyte. Although peak selection can be done by eye, software is typically used to automate the detection of peaks (Ciphergen's ProteinChip® software). In general, this software functions by identifying signals having a signal-to-noise ratio above a selected threshold and labeling the mass of the peak at the center of the peak signal. One version of this software clusters all peaks appearing in the various spectra within a defined mass range, and assigns a mass (m/z) to all the peaks that are near the mid-point of the mass (m/z) cluster.

As used herein, "polypeptide" includes proteins, fragments of proteins, and peptides, whether isolated from natural sources, produced by recombinant techniques or chemically synthesized. Polypeptides of the invention typically comprise at least about 6 amino acids.

As used herein, "tumor protein" is a protein that is expressed by tumor cells. Proteins that are tumor proteins also react detectably within an immunoassay (such as an ELISA) with antisera from a patient with cancer.

An "immunogenic polypeptide," as used herein is a portion of a protein that is recognized (i.e., specifically bound) by a B-cell and/or T-cell surface antigen receptor. Such immunogenic polypeptides generally comprise at least 5 amino acid residues, more preferably at least 10, and still more preferably at least 20 amino acid residues of a protein associated with cancer or infectious disease. Certain preferred immunogenic polypeptides include peptides in which an N-terminal leader sequence and/or transmembrane domain have been deleted. Other preferred immunogenic polypeptides may contain a small N- and/or C-terminal deletion (e.g., 1-30 amino acids, preferably 5-15 amino acids), relative to the mature protein.

As used herein, "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

The term "nucleic acid" or "polynucleotide" refers to a deoxyribonucleotide or ribonucleotide polymer in either single- or double-stranded form, and unless otherwise limited, encompasses known analogs of natural nucleotides that hybridize to nucleic acids in a manner similar to naturally-occurring nucleotides.

As used herein, "antigen-presenting cell" or "APC" means a cell capable of handling and presenting antigen to a lymphocyte. Examples of APCs include, but are not limited to, macrophages, Langerhans-dendritic cells, follicular dendritic cells, B cells, monocytes, fibroblasts and fibrocytes. Dendritic cells are a preferred type of antigen presenting cell. Dendritic cells are found in many non-lymphoid tissues but can migrate via the afferent lymph or the blood stream to the T-dependent areas of lymphoid organs. In non-lymphoid organs, dendritic cells include Langerhans cells and interstitial dendritic cells. In the lymph and blood, they include afferent lymph veiled cells and blood dendritic cells, respectively. In lymphoid organs, they include lymphoid dendritic cells and interdigitating cells.

As used herein, "modified" to present an epitope refers to antigen-presenting cells (APCs) that have been manipulated to present an epitope by natural or recombinant methods. For example, the APCs can be modified by exposure to the isolated antigen, alone or as part of a mixture, peptide loading, or by genetically modifying the APC to express a polypeptide that includes one or more epitopes.

As used herein, "pharmaceutically acceptable carrier" includes any material which, when combined with an active ingredient, allows the ingredient to retain biological activity and is non-reactive with the subjects immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline.

Compositions comprising such carriers are formulated by well known conventional methods (see, for example, *Remington's Pharmaceutical Sciences*, 18th edition, A. Gennaro, ed., Mack Publishing Co., Easton, Pa., 1990).

As used herein, "a" or "an" means at least one, unless clearly indicated otherwise.

Diagnostic Methods

The invention provides a method for detecting cancer in a specimen comprising analyzing the specimen for the presence of an OC molecule or biomarker. Also provided is a method of screening for cancer in a subject. The cancer of interest is typically ovarian or endometrial cancer. In one embodiment, the method comprises contacting a specimen or tissue sample from the subject to be screened with a molecule that recognizes and binds an OC molecule. The molecule can be, for example, an antibody directed against an OC peptide, or an oligonucleotide probe or antisense molecule directed against an OC nucleic acid molecule. The specimen can be from a mammal, such as human, bovine, equine, canine, feline, porcine, and ovine tissue. The subject is preferably a human, typically a woman who would benefit from knowledge of her ovarian or endometrial cancer status. The specimen can comprise serum, blood, plasma, vaginal secretions, urine, saliva, tears, a tumor specimen, or other suitable specimen.

Some OC biomarkers are present at increased levels in neoplastic versus normal tissue samples, or in malignant versus non-malignant tissue samples, while others are absent or down-regulated in these conditions. The data shown in Example 3 below provides an overview of OC biomarkers and their relative levels observed in normal, neoplastic, malignant and non-malignant specimens. Depending on the particular assay employed in the method of the invention, the detecting or screening can be determined by presence or absence of the relevant OC biomarker(s), or by up-regulation or down-regulation relative to normal or non-malignant specimens. Up-regulation or down-regulation can be determined on the basis of a statistically significant increase or decrease in level of the biomarker, or by a two-fold or greater increase or decrease in the level of biomarker detected in the sample relative to the normal or non-malignant sample.

In one embodiment, the method comprises use of an immunoassay, such as an ELISA type assay, that employs an OC antibody to detect the presence (or up-regulation or down-regulation) of OC in a specimen. Other assays include a radioimmune assay (RIA), a Western blot assay, or a slot blot assay. The immunoassay can be used either as a simple detection method, or to measure the amount or level of OC biomarker present. Such measurements can be quantitative, by comparing measured amounts to a known or control amount of the biomarker, or can be used to compare relative amounts between different specimens or samples. The antibody can be immobilized on a substrate. The amount or presence of biomarker is typically determined via assay directed to a detectable marker or other indication of binding of the antibody to biomarker. Measures can be based on, for example, detection of fluorescence, luminescence, chemiluminescence, absorbance, reflectance, transmittance, birefringence or refractive index (e.g., surface plasmon resonance, ellipsometry, a resonant mirror method, a grating coupler waveguide method or interferometry). Optical methods include microscopy (both confocal and non-confocal), imaging methods and non-imaging methods. Electrochemical methods include voltametry and amperometry methods. Radio frequency methods include multipolar resonance spectroscopy. Methods for performing these assays are readily known in the art. Other methods can be used to detect the presence or amount of a biomarker in a sample. Typically, the biomarker is first captured on a substrate. Examples of such methods include, but are not limited to, gas phase ion spectrometry methods, optical methods, electrochemical methods, atomic force microscopy and radio frequency methods. In one embodiment, the method comprises mass spectrometry, such as "surface-enhanced laser desorption/ionization" or "SELDI". SELDI refers to a method of desorption/ionization gas phase ion spectrometry (e.g., mass spectrometry) in which the analyte is captured on the surface of a SELDI probe that engages the probe interface. In "SELDI-MS," the gas phase ion spectrometer is a mass spectrometer.

Those skilled in the art will appreciate additional variations suitable for the method of detecting cancer in tissue through detection of an OC molecule in a specimen. This method can also be used to monitor OC levels in tissue of a patient undergoing treatment for cancer. The suitability of an OC-targeted therapeutic regimen for initial or continued treatment can be determined by monitoring OC levels using this method.

The invention additionally provides a method for identifying a molecule that inhibits proliferation of cancer cells. The method comprises contacting a candidate molecule with an OC molecule and determining whether the candidate molecule disrupts the biological activity of the OC molecule. Disruption of the biological activity of the OC molecule is indicative of a molecule that inhibits proliferation of cancer cells. Representative OC molecules include antibodies, proteins and nucleotides.

Kits

For use in the diagnostic and therapeutic applications described herein, kits are also within the scope of the invention. Such kits can comprise a carrier, package or container that is compartmentalized to receive one or more containers such as vials, tubes, and the like, each of the container(s) comprising one of the separate elements to be used in the method. For example, the container(s) can comprise a probe that is or can be detectably labeled. The probe can be an antibody or polynucleotide specific for an OC protein or an OC gene or message, respectively. Alternatively, the kit can comprise a mass spectrometry (MS) probe. The kit can also include containers containing nucleotide(s) for amplification or silencing of a target nucleic acid sequence, and/or a container comprising a reporter-means, such as a biotin-binding protein, e.g., avidin or streptavidin, bound to a detectable label, e.g., an enzymatic, florescent, or radioisotope label. The kit can include all or part of the amino acid sequence of the OC, or a nucleic acid molecule that encodes such amino acid sequences.

The kit of the invention will typically comprise the container described above and one or more other containers comprising materials desirable from a commercial and user standpoint, including buffers, diluents, filters, needles, syringes, and package inserts with instructions for use. In addition, a label can be provided on the container to indicate that the composition is used for a specific therapeutic or non-therapeutic application, and can also indicate directions for either in vivo or in vitro use, such as those described above. Directions and or other information can also be included on an insert which is included with the kit.

Polynucleotides of the Invention

The invention provides polynucleotides that encode one or more OC polypeptides, or a portion or other variant thereof. Preferred polynucleotides comprise at least 15 consecutive nucleotides, preferably at least 30 consecutive nucleotides and more preferably at least 45 consecutive nucleotides, that encode an OC polypeptide. Polynucleotides that are fully complementary to any such sequences are also encompassed by the present invention. Polynucleotides may be single-stranded (coding or antisense) or double-stranded, and may be DNA (genomic, cDNA or synthetic) or RNA molecules, including siRNA. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials. Portions of such OC polynucleotides can be useful as primers and probes for the amplification and detection of OC related molecules in tissue specimens.

Polynucleotides may comprise a native sequence (i.e., an endogenous sequence that encodes an OC polypeptide or a portion thereof) or may comprise a variant of such a sequence. Polynucleotide variants contain one or more substitutions, additions, deletions and/or insertions such that the immunogenicity of the encoded polypeptide is not diminished, relative to a native OC protein. Variants preferably exhibit at least about 70% identity, more preferably at least about 80% identity and most preferably at least about 90% identity to a polynucleotide sequence that encodes a native OC protein or a portion thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626-645 Methods in Enzymology vol. 183, Academic Press, Inc., San Diego, Calif.; Higgins, D. G. and Sharp, P. M. (1989) CABIOS 5:151-153; Myers, E. W. and Muller W. (1988) CABIOS 4:11-17; Robinson, E. D. (1971) Comb. Theor. 11:105; Santou, N., Nes, M. (1987) Mol. Biol. Evol. 4:406-425; Sneath, P. H. A. and Sokal, R. R. (1973) Numerical Taxonomy the Principles and Practice of Numerical Taxonomy, Freeman Press, San Francisco, Calif.; Wilbur, W. J. and Lipman, D. J. (1983) Proc. Natl. Acad. Sci. USA 80:726-730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native OC protein (or a complementary sequence).

Suitable "moderately stringent conditions" include prewashing in a solution of 5×SSC, 0.5% SDS, 1.0 mM EDTA (pH 8.0); hybridizing at 50° C.-65° C., 5×SSC, overnight; followed by washing twice 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Polynucleotides may be prepared using any of a variety of techniques known in the art. DNA encoding an OC protein may be obtained From a cDNA library prepared from tissue expressing an OC protein mRNA. Accordingly, human OC DNA can be conveniently obtained from a cDNA library prepared from human tissue. The OC protein-encoding gene may also be obtained from a genomic library or by oligonucleotide synthesis. Libraries can be screened with probes (such as antibodies to OC or oligonucleotides of at least about 20-80 bases) designed to identify the gene of interest or the protein encoded by it. Screening the cDNA or genomic library with the selected probe may be conducted using standard procedures, such as those described in Sambrook et al., *Molecular Cloning: A Laboratory Manual* (New York: Cold Spring Harbor Laboratory Press, 1989). An alternative means to isolate the gene encoding OC is to use PCR methodology (Sambrook et al., supra; Dieffenbach et al., *PCR Primer: A Laboratory Manual* (Cold Spring Harbor Laboratory Press, 1995)).

The oligonucleotide sequences selected as probes should be sufficiently long and sufficiently unambiguous that false positives are minimized. The oligonucleotide is preferably labeled such that it can be detected upon hybridization to DNA in the library being screened. Methods of labeling are well known in the art, and include the use of radiolabels, such as $^{32}$P-labeled ATP, biotinylation or enzyme labeling. Hybridization conditions, including moderate stringency and high stringency, are provided in Sambrook et al., supra.

Polynucleotide variants may generally be prepared by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis (see Adelman et al., DNA 2:183, 1983). Alternatively, RNA molecules may be generated by in vitro or in vivo transcription of DNA sequences encoding an OC protein, or portion thereof, provided that the DNA is incorporated into a vector with a suitable RNA polymerase promoter (such as T7 or SP6). Certain portions may be used to prepare an encoded polypeptide, as described herein. In addition, or alternatively, a portion may be administered to a patient such that the encoded polypeptide is generated in vivo (e.g., by transfecting antigen-presenting cells, such as dendritic cells, with a cDNA construct encoding an OC polypeptide, and administering the transfected cells to the patient).

Any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl-methyl-, thio- and other modified forms of adenine, cytidine, guanine, thymine and uridine.

Nucleotide sequences can be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

Within certain embodiments, polynucleotides may be formulated so as to permit entry into a cell of a mammal, and to permit expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g., avian pox virus). Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art.

Other formulations for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Antisense Molecules

The antisense molecules of the present invention comprise a sequence substantially complementary, or preferably fully complementary, to all or a fragment of an OC gene. Included are fragments of oligonucleotides within the coding sequence of an OC gene. Antisense oligonucleotides of DNA or RNA complementary to sequences at the boundary between introns and exons can be employed to prevent the maturation of newly-generated nuclear RNA transcripts of specific genes into mRNA for transcription. Antisense RNA complimentary to specific genes can hybridize with the mRNA for that gene and prevent its translation. The antisense molecule can be DNA, RNA, or a derivative or hybrid thereof. Examples of such derivative molecules include, but are not limited to, peptide nucleic acid (PNA) and phosphorothioate-based molecules such as deoxyribonucleic guanidine (DNG) or ribonucleic guanidine (RNG).

Antisense RNA can be provided to the cell as "ready-to-use" RNA synthesized in vitro or as an antisense gene stably transfected into cells which will yield antisense RNA upon transcription. Hybridization with mRNA results in degradation of the hybridized molecule by RNAse H and/or inhibition of the formation of translation complexes. Both result in a failure to produce the product of the original gene.

Both antisense RNA and DNA molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro or in vivo transcription of DNA sequences encoding the antisense RNA molecule. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

DNA molecules may be modified to increase intracellular stability and half-life. Possible modifications include, but are not limited to, the addition of flanking sequences of the 5' and/or 3' ends of the molecule or the use of phosphorothioate or 2' O-methyl rather than phosphodiesterase linkages within the backbone of the molecule. Other modifications include the use of chimeric antisense compounds. Chimeric antisense compounds of the invention may be formed as composite structures of two or more oligonucleotides, modified oligonucleotides, oligonucleosides and/or oligonucleotide mimetics. Such compounds have also been referred to in the art as hybrids or gapmers. Representative United States patents that teach the preparation of such hybrid structures include, but are not limited to, U.S. Pat. Nos. 5,700,922 and 6,277,603.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Antisense compositions of the invention include oligonucleotides formed of homopyrimidines that can recognize local stretches of homopurines in the DNA double helix and bind to them in the major groove to form a triple helix. See: Helen, C and Toulme, J J. Specific regulation of gene expression by antisense, sense, and antigene nucleic acids. Biochem. Biophys Acta, 1049:99-125, 1990. Formation of the triple helix would interrupt the ability of the specific gene to undergo transcription by RNA polymerase. Triple helix formation using myc-specific oligonucleotides has been observed. See: Cooney, M, et al. Science 241:456-459.

Antisense sequences of DNA or RNA can be delivered to cells. Several chemical modifications have been developed to prolong the stability and improve the function of these molecules without interfering with their ability to recognize specific sequences. These include increasing their resistance to degradation by DNases, including phosphotriesters, methylphosphonates, phosphorothioates, alpha-anomers, increasing their affinity for binding partners by covalent linkage to various intercalating agents such as psoralens, and increasing uptake by cells by conjugation to various groups including polylysine. These molecules recognize specific sequences encoded in mRNA and their hybridization prevents translation of and increases the degradation of these messages.

Antisense compositions including oligonucleotides, derivatives and analogs thereof, conjugation protocols, and antisense strategies for inhibition of transcription and translation are generally described in: Antisense Research and Applications, Crooke, S. and B. Lebleu, eds. CRC Press, Inc. Boca Raton Fla. 1993; Nucleic Acids in Chemistry and Biology Blackburn, G. and M. J. Gait, eds. IRL Press at Oxford University Press, Inc. New York 1990; and Oligonucleotides and Analogues: A Practical Approach Eckstein, F. ed., IRL Press at Oxford University Press, Inc. New York 1991; which are each hereby incorporated herein by reference including all references cited therein which are hereby incorporated herein by reference.

RNA Interference

Long double-stranded RNAs (dsRNAs; typically >200 nt) can be used to silence the expression of a target gene. The dsRNAs enter a cellular pathway that is commonly referred to as the RNA interference (RNAi) pathway. First, the dsRNAs get processed into 20-25 nucleotide (nt) small interfering RNAs (siRNAs) by an RNase III-like enzyme called Dicer (initiation step). Then, the siRNAs assemble into endoribonuclease-containing complexes known as RNA-induced silencing complexes (RISCs), unwinding in the process. The siRNA strands subsequently guide the RISCs to complementary RNA molecules, where they cleave and destroy the cognate RNA (effecter step). Cleavage of cognate RNA takes place near the middle of the region bound by the siRNA strand.

In mammalian cells, introduction of long dsRNA (>30 nt) initiates a potent antiviral response, exemplified by nonspecific inhibition of protein synthesis and RNA degradation. The mammalian antiviral response can be bypassed, however, by the introduction or expression of siRNAs (Ambion, Inc., Austin, Tex.).

OC Polypeptides

OC polypeptides as described herein may be of any length. Exemplary lengths include, but are not limited to, up to 10, 15, 20, 25, 30, 40, 50, 60, 70, 80, 90 and 100 amino acids or more. Additional sequences derived from the native protein and/or heterologous sequences may be present, and such sequences may, but need not, possess further ligand binding, immunogenic or antigenic properties. Those skilled in the art will appreciate that other portions or variants thereof will be useful in the treatment and detection of cancer.

Immunogenic polypeptides may generally be identified using well known techniques, such as those summarized in Paul, Fundamental Immunology, 4th ed., 663-665 (Lippincott-Raven Publishers, 1999) and references cited therein. Such techniques include screening polypeptides for the ability to react with antigen-specific antibodies, antisera and/or T-cell lines or clones. As used herein, antisera and antibodies are antigen-specific if they specifically bind to an antigen (i.e., they react with the protein in an ELISA or other immunoassay, and do not react detectably with unrelated proteins). Such antisera and antibodies may be prepared using well known techniques. An immunogenic polypeptide can be a portion of a native protein that reacts with such antisera and/or T-cells at a level that is not substantially less than the reactivity of the full length polypeptide (e.g., in an ELISA and/or T-cell reactivity assay). Such immunogenic portions may react within such assays at a level that is similar to or greater than the reactivity of the full length polypeptide. Such screens may generally be performed using methods well known to those of ordinary skill in the art, such as those described in Harlow and Lane, Antibodies: A Laboratory Manual, Cold Spring Harbor Laboratory, 1988. For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

An OC polypeptide of the invention can comprise a variant of a native OC protein. A polypeptide "variant," as used herein, is a polypeptide that differs from a native OC protein in one or more substitutions, deletions, additions and/or insertions, such that the immunogenicity of the polypeptide is not substantially diminished. In other words, the ability of a variant to react with antigen-specific antisera may be enhanced or unchanged, relative to the native protein, or may be diminished by less than 50%, and preferably less than 20%, relative to the native protein. Such variants may generally be identified by modifying one of the above polypeptide sequences and evaluating the reactivity of the modified polypeptide with antigen-specific antibodies or antisera as described herein. Preferred variants include those in which one or more portions, such as an N-terminal leader sequence, have been removed. Other preferred variants include variants in which a small portion (e.g., 1-30 amino acids, preferably 5-15 amino acids) has been removed from the N- and/or C-terminal of the mature protein. Polypeptide variants preferably exhibit at least about 70%, more preferably at least about 90% and most preferably at least about 95% identity (determined as described above) to the identified polypeptides.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

Polypeptides may comprise a signal (or leader) sequence at the N-terminal end of the protein that co-translationally or post-translationally directs transfer of the protein. The polypeptide may also be conjugated to a linker or other sequence for ease of synthesis, purification or identification of the polypeptide (e.g., poly-FEs), or to enhance binding of the polypeptide to a solid support. For example, a polypeptide may be conjugated to an immunoglobulin Fc region.

In some embodiments, the polypeptides are purified from the same subject to whom the composition will be administered. In these embodiments, it may be desirable to increase the number of tumor or infected cells. Such a scale up of cells could be performed in vitro or in zivo, using, for example, a SCID mouse system. Where the cells are scaled up in the presence of non-human cells, such as by growing a human subject's tumor in a SCID mouse host, care should be taken to purify the human cells from any non-human (e.g., mouse) cells that may have infiltrated the tumor. In these embodiments in which the composition will be administered to the same subject from whom the polypeptides are purified, it may also be desirable purify several OC polypeptides to optimize the efficacy of a limited quantity of starting material.

Recombinant polypeptides encoded by DNA sequences as described above may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are E. coli, yeast, insect cells or a mammalian cell line such as COS or CHO. Supernatants from suitable host/vector systems that secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Portions and other variants having fewer than about 100 amino acids, and generally fewer than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, J. Am. Chem. Soc. 85:2149-2146, 1963. Equipment for automated synthesis of polypeptides is commercially available from suppliers such as Perkin Elmer/Applied BioSystems Division (Foster City, Calif.), and may be operated according to the manufacturer's instructions.

Polypeptides can be synthesized on a Perkin Elmer/Applied Biosystems Division 430A peptide synthesizer using FMOC chemistry with HPTU (O-BenzotriazoleN,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%-60% acetonitrile (containing 0.1% TFA) in water may be used to elute the peptides. Following lyophilization of the pure fractions, the peptides may be characterized using electrospray or other types of mass spectrometry and by amino acid analysis.

Fusion Proteins

In some embodiments, the polypeptide is a fusion protein that comprises multiple polypeptides as described herein, or that comprises at least one polypeptide as described herein and an unrelated sequence. In some embodiments, the fusion protein comprises an OC polypeptide and an immunogenic polypeptide. The immunogenic polypeptide can comprise, for example, all or a portion of an additional tumor protein.

Additional fusion partners can be added. A fusion partner may, for example, serve as an immunological fusion partner by assisting in the provision of T helper epitopes, preferably T helper epitopes recognized by humans. As another example, a fusion partner may serve as an expression enhancer, assisting in expressing the protein at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and the second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., Gene 40:39-46, 1985; Murphy et al., Proc. Natl. Acad. Sci. USA 83:8258-8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located 5' to the DNA sequence encoding the first polypeptides. Similarly, stop codons required to end translation and transcription termination signals are present 3' to the DNA sequence encoding the second polypeptide.

Fusion proteins are also provided that comprise a polypeptide of the present invention together with an unrelated immunogenic protein. Preferably the immunogenic protein is capable of eliciting a memory response. Examples of such proteins include tetanus, tuberculosis and hepatitis proteins (see, for example, Stoute et al., New Engl. J. Med. 336:86-91, 1997).

Within preferred embodiments, an immunological fusion partner is derived from protein D, a surface protein of the gram-negative bacterium Haemophilus influenza B (WO 91/18926). Preferably, a protein D derivative comprises approximately the first third of the protein (e.g., the first N-terminal 100-110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS I (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; Gene 43:265-292, 1986). LYTA is an autolysin that specifically degrades certain bonds in the peptidoglycan backbone. The C-terminal domain of the LYTA protein is responsible for the affinity to the choline or to some choline analogues such as DEAR This property has been exploited for the development of *E. coli* C-LYTA expressing plasmids useful for expression of fusion proteins. Purification of hybrid proteins containing the C-LYTA fragment at the amino terminus has been described (see Biotechnology 10:795-798, 1992). Within a preferred embodiment, a repeat portion of LYTA may be incorporated into a fusion protein. A repeat portion is found in the C-terminal region starting at residue 178. A particularly preferred repeat portion incorporates residues 188-305.

In general, polypeptides (including fusion proteins) and polynucleotides as described herein are isolated. An "isolated" polypeptide or polynucleotide is one that is removed from its original environment. For example, a naturally occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Antibodies

The term "antibody" is used in the broadest sense and specifically covers single anti-OC monoclonal antibodies (including agonist, antagonist and neutralizing antibodies) and anti-OC antibody compositions with polyepitopic specificity. The term "monoclonal antibody" (mAb) as used herein refers to an antibody obtained from a population of substantially homogeneous antibodies, i.e. the antibodies comprising the individual population are identical except for possible naturally-occurring mutations that may be present in minor amounts.

The invention provides antibodies that bind to OC proteins and polypeptides. The most preferred antibodies will specifically bind to an OC protein and will not bind (or will bind weakly) to non-OC proteins and polypeptides. An antibody "specifically binds" to a protein (or peptide) if it is capable of a binding reaction with that protein that is determinative of the presence of the protein in a heterogeneous population of proteins and other biologics. For example, the antibody binds to a particular protein at least two times as much as to the background and does not substantially bind in a significant amount to other proteins present in the sample.

Anti-OC antibodies that are particularly contemplated include monoclonal and polyclonal antibodies as well as fragments containing the antigen binding domain and/or one or more complementarity determining regions of these antibodies. As used herein, an antibody fragment is defined as at least a portion of the variable region of the immunoglobulin molecule that binds to its target, i.e., the antigen binding region.

OC antibodies of the invention may be particularly useful in cancer diagnostic and prognostic assays, and imaging methodologies. Intracellularly expressed antibodies (e.g., single chain antibodies) may be therapeutically useful in treating cancers in which the expression of OC is involved, such as for example advanced and metastatic brain cancers, as well as cancers of the lung, breast, colon or prostate. Also useful in therapeutic methods for treatment of cancer are systemically administered OC antibodies that interfere with OC function or that target cells expressing OC for delivery of a toxin or therapeutic molecule. Such delivery of a toxin or therapeutic molecule can be achieved using known methods of conjugating a second molecule to the OC antibody or fragment thereof. Similarly, such antibodies may be useful in the treatment, diagnosis, and/or prognosis of other cancers, to the extent OC is also expressed or overexpressed in other types of cancer.

The invention also provides various immunological assays useful for the detection and quantification of OC polypeptides. Such assays generally comprise one or more OC antibodies capable of recognizing and binding an OC, and may be performed within various immunological assay formats well known in the art, including but not limited to various types of radioimmunoassays, enzyme-linked immunosorbent assays (ELISA), enzyme-linked immunofluorescent assays (ELIFA), and the like. In addition, immunological imaging methods capable of detecting cancers expressing OC are also provided by the invention, including but not limited to radioscintigraphic imaging methods using labeled OC antibodies. Such assays may be clinically useful in the detection, monitoring, and prognosis of OC expressing cancers.

Various methods for the preparation of antibodies are well known in the art. For example, antibodies may be prepared by immunizing a suitable mammalian host using an OC protein, peptide, or fragment, in isolated or immunoconjugated form (Antibodies: A Laboratory Manual, CSH Press, Eds., Harlow, and Lane (1988): Harlow, Antibodies, Cold Spring Harbor Press, NY (1989)). In addition, fusion proteins of OC may also be used, such as an OC GST-fusion protein. In another embodiment, an OC peptide may be synthesized and used as an immunogen.

The antibodies or fragments may also be produced, using current technology, by recombinant means. Regions that bind specifically to the desired regions of the OC protein can also be produced in the context of chimeric or CDR grafted antibodies of multiple species origin. Humanized or human OC antibodies may also be produced and are preferred for use in therapeutic contexts. Methods for humanizing murine and other non-human antibodies by substituting one or more of the non-human antibody CDRs for corresponding human antibody sequences are well known (see for example, Jones et al., 1986, Nature 321: 522-525; Riechmann et al., 1988, Nature 332: 323-327; Verhoeyen et al., 1988, Science 239: 1534-1536). See also, Carter et al., 1993, Proc. Natl. Acad. Sci. USA 89: 4285 and Sims et al., 1993, J. Immunol. 151: 2296. Methods for producing fully human monoclonal antibodies include phage display and transgenic methods (for review, see Vaughan et al., 1998, Nature Biotechnology 16: 535-539).

Fully human OC monoclonal antibodies may be generated using cloning technologies employing large human Ig gene combinatorial libraries (i.e., phage display) (Griffiths and Hoogenboom, Building an in vitro immune system:

human antibodies from phage display libraries. In: Protein Engineering of Antibody Molecules for Prophylactic and Therapeutic Applications in Man. Clark, M. (Ed.), Nottingham Academic, pp 45-64 (1993); Burton and Barbas, Human Antibodies from combinatorial libraries. Id., pp 65-82). Fully human OC monoclonal antibodies may also be produced using transgenic mice engineered to contain human immunoglobulin gene loci as described in PCT Patent Application WO98/24893, Kucherlapati and Jakobovits et al., published Dec. 3, 1997 (see also, Jakobovits, 1998, Exp. Opin. Invest. Drugs 7(4): 607-614). This method avoids the in vitro manipulation required with phage display technology and efficiently produces high affinity authentic human antibodies.

Reactivity of OC antibodies with an OC protein may be established by a number of well known means, including western blot, immunoprecipitation, ELISA, and FACS analyses using, as appropriate, OC proteins, peptides, OC-expressing cells or extracts thereof.

An OC antibody or fragment thereof of the invention may be labeled with a detectable marker or conjugated to a second molecule. Suitable detectable markers include, but are not limited to, a radioisotope, a fluorescent compound, a bioluminescent compound, chemiluminescent compound, a metal chelator or an enzyme. A second molecule for conjugation to the OC antibody can be selected in accordance with the intended use. For example, for therapeutic use, the second molecule can be a toxin or therapeutic agent. Further, bi-specific antibodies specific for two or more OC epitopes may be generated using methods generally known in the art. Homodimeric antibodies may also be generated by cross-linking techniques known in the art (e.g., Wolff et al., Cancer Res. 53: 2560-2565).

T Cells

Immunotherapeutic compositions may also, or alternatively, comprise T cells specific for an OC polypeptide. Such cells may generally be prepared in vitro or ex vivo, using standard procedures. For example, T cells may be isolated from bone marrow, peripheral blood, or a fraction of bone marrow or peripheral blood of a patient, using a commercially available cell separation system, such as the ISOLEX™ magnetic cell selection system, available from Nexell Therapeutics, Irvine, Calif. (see also U.S. Pat. No. 5,536,475); or MACS cell separation technology from Miltenyi Biotec, including Pan T Cell Isolation Kit, CD4+ T Cell Isolation Kit, and CD8+ T Cell Isolation Kit (see also U.S. Pat. No. 5,240,856; U.S. Pat. No. 5,215,926; WO 89/06280; WO 91/16116 and WO 92/07243). Alternatively, T cells may be derived from related or unrelated humans, non-human mammals, cell lines or cultures.

T cells may be stimulated with an OC polypeptide, polynucleotide encoding an OC polypeptide and/or an antigen presenting cell (APC) that expresses such an OC polypeptide. The stimulation is performed under conditions and for a time sufficient to permit the generation of T cells that are specific for the polypeptide. Preferably, an OC polypeptide or polynucleotide is present within a delivery vehicle, such as a microsphere, to facilitate the generation of specific T cells.

T cells are considered to be specific for an OC polypeptide if the T cells kill target cells coated with the polypeptide or expressing a gene encoding the polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., Cancer Res. 54:1065-1070, 1994.

Detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with an OC protein (100 ng/ml-100 µg/ml, preferably 200 ng/ml-25 µg/ml) for 3-7 days should result in at least a two fold increase in proliferation of the T cells. Contact as described above for 2-3 hours should result in activation of the T cells, as measured using standard cytokine assays in which a two fold increase in the level of cytokine release (e.g., TNF or IFN-γ) is indicative of T cell activation (see Coligan et al., Current Protocols in Immunology, vol. 1, Wiley Interscience (Greene 1998)). T cells that have been activated in response to an OC polypeptide, polynucleotide or polypeptide-expressing APC may be CD4+ and/or CD8+. T cells can be expanded using standard techniques.

Within preferred embodiments, the T cells are derived from either a patient or a related, or unrelated, donor and are administered to the patient following stimulation and expansion. For therapeutic purposes, CD4+ or CD8+ T cells that proliferate in response to an OC polypeptide, polynucleotide or APC can be expanded in number either in vitro or in vivo. Proliferation of such T cells in vitro may be accomplished in a variety of ways. For example, the T cells can be re-exposed to an OC polypeptide, with or without the addition of T cell growth factors, such as interleukin-2, and/or stimulator cells. Alternatively, one or more T cells that proliferate in the presence of an OC polypeptide can be expanded in number by cloning. Methods for cloning cells are well known in the art, and include limiting dilution.

Pharmaceutical Compositions and Vaccines

The invention provides OC polypeptide, polynucleotides, T cells and/or antigen presenting cells that are incorporated into pharmaceutical compositions, including immunogenic compositions (i.e., vaccines). Pharmaceutical compositions comprise one or more such compounds and, optionally, a physiologically acceptable carrier. Vaccines may comprise one or more such compounds and an adjuvant that serves as a non-specific immune response enhancer. The adjuvant may be any substance that enhances an immune response to an exogenous antigen. Examples of adjuvants include conventional adjuvants, biodegradable microspheres (e.g., polylactic galactide), immunostimulatory oligonucleotides and liposomes (into which the compound is incorporated; see e.g., Fullerton, U.S. Pat. No. 4,235,877). Vaccine preparation is generally described in, for example, M. F. Powell and M. J. Newman, eds., "Vaccine Design (the subunit and adjuvant approach)," Plenum Press (NY, 1995). Pharmaceutical compositions and vaccines within the scope of the present invention may also contain other compounds that may be biologically active or inactive. For example, one or more immunogenic portions of other tumor antigens may be present, either incorporated into a fusion polypeptide or as a separate compound, within the composition or vaccine.

A pharmaceutical composition or vaccine can contain DNA encoding one or more of the polypeptides as described above, such that the polypeptide is generated in situ. As noted above, the DNA may be present within any of a variety of delivery systems known to those of ordinary skill in the art, including nucleic acid expression systems, bacteria and viral expression systems. Numerous gene delivery techniques are well known in the art, such as those described by Rolland, Crit. Rev. Therap. Drug Carrier Systems 15:143-

198, 1998, and references cited therein. Appropriate nucleic acid expression systems contain the necessary DNA sequences for expression in the patient (such as a suitable promoter and terminating signal). Bacterial delivery systems involve the administration of a bacterium (such as *Bacillus-Calmette-Guenin*) that expresses an immunogenic portion of the polypeptide on its cell surface or secretes such an epitope.

In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., Proc. Natl. Acad. Sci. USA 86:317-321, 1989; Flexner et al., Ann. N. Y. Acad Sci. 569:86-103, 1989; Flexner et al., Vaccine 8:17-21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner-Biotechniques 6:616-627, 1988; Rosenfeld et al., Science 252:431-434, 1991; Kolls et al., Proc. Natl. Acad. Sci. USA 91:215-219, 1994; Kass-Eisler et al., Proc. Natl. Acad. Sci. USA 90:11498-11502, 1993; Guzman et al., Circulation 88:2838-2848, 1993; and Guzman et al., Cir. Res. 73:1202-1207, 1993. Techniques for incorporating DNA into such expression systems are well known to those of ordinary skill in the art. The DNA may also be "naked," as described, for example, in Ulmer et al., Science 259:1745-1749, 1993 and reviewed by Cohen, Science 259:1691-1692, 1993. The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous, intradermal or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

In addition, the carrier may contain other pharmacologically-acceptable excipients for modifying or maintaining the pH, osmolarity, viscosity, clarity, color, sterility, stability, rate of dissolution, or odor of the formulation. Similarly, the carrier may contain still other pharmacologically-acceptable excipients for modifying or maintaining the stability, rate of dissolution, release, or absorption or penetration across the blood-brain barrier of the OC related molecule. Such excipients are those substances usually and customarily employed to formulate dosages for parenteral administration in either unit dose or multi-dose form or for direct infusion into the CSF by continuous or periodic infusion from an implanted pump.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alternatively, compositions of the present invention may be formulated as a lyophilizate. Compounds may also be encapsulated within liposomes using well known technology.

Any of a variety of adjuvants may be employed in the vaccines of this invention. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); aluminum salts such as aluminum hydroxide gel (alum) or aluminum phosphate; salts of calcium, iron or zinc; an insoluble suspension of acylated tyrosine acylated sugars; cationically or anionically derivatized polysaccharides; polyphosphazenes biodegradable microspheres; monophosphoryl lipid A and quil A. Cytokines, such as GM CSF or interleukin-2, -7, or -12, may also be used as adjuvants.

Within the vaccines provided herein, the adjuvant composition is preferably designed to induce an immune response predominantly of the Th1 type. High levels of Th1-type cytokines (e.g., IFN-α, IL-2 and IL-12) tend to favor the induction of cell mediated immune responses to an administered antigen. In contrast, high levels of Th2-type cytokines (e.g., IL-4, IL-5, IL-6, IL-10 and TNF-β) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, Ann. Rev. Immunol. 7:145-173, 1989.

The compositions described herein may be administered as part of a sustained release formulation (i.e., a formulation such as a capsule or sponge that effects a slow release of compound following administration). Such formulations may generally be prepared using well known technology and administered by, for example, oral, rectal or subcutaneous implantation, or by implantation at the desired target site, such as a site of surgical excision of a tumor. Sustained-release formulations may contain a polypeptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

Antigen Presenting Cells

Any of a variety of delivery vehicles may be employed within pharmaceutical compositions and vaccines to facilitate production of an antigen-specific immune response that targets tumor cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor or anti-infective effects per se and/or to be immunologically compatible with the receiver (i.e., matched BLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, Nature 392:245-251, 1998) and have been shown to be effective as a physiological adjuvant for eliciting prophylactic or therapeutic antitumor immunity (see Timmerman and Levy, Ann. Rev. Med. 50:507-529, 1999). In general, dendritic cells may be identified based on their typical shape (stellate in situ, with marked cytoplasmic processes (dendrites) visible in vitro) and based on the lack of differentiation markers of B cells (CD19 and CD20), T cells (CD3), monocytes (CD14) and natural killer cells (CD56), as determined using standard assays. Dendritic cells may, of course, be engineered to express specific cell surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., Nature Med. 4:594-600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor, mannose receptor and DEC-205 marker. The mature phenotype is typically characterized by a lower expression of these markers, but a high expression of cell surface molecules responsible for T cell activation such as class I and class II NMC, adhesion molecules (e.g., CD54 and CD11) and costimulatory molecules (e.g., CD40, CD80 and CD86).

APCs may generally be transfected with a polynucleotide encoding an OC polypeptide (or portion or other variant thereof) such that the OC polypeptide, or an immunogenic portion thereof, is expressed on the cell surface. Such transfection may take place ex vivo, and a composition or vaccine comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., Immunology and Cell Biology 75:456-460, 1997. Antigen loading of dendritic cells may be achieved by incubating dendritic cells or progenitor cells with the OC polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

Therapeutic and Prophylactic Methods

Treatment includes prophylaxis and therapy. Prophylaxis or therapy can be accomplished by a single direct injection at a single time point or multiple time points to a single or multiple sites. Administration can also be nearly simultaneous to multiple sites. Patients or subjects include mammals, such as human, bovine, equine, canine, feline, porcine, and ovine animals. The subject is preferably a human.

A cancer may be diagnosed using criteria generally accepted in the art, including the presence of a malignant tumor. Pharmaceutical compositions and vaccines may be administered either prior to or following surgical removal of primary tumors and/or treatment such as administration of radiotherapy or conventional chemotherapeutic drugs.

Within certain embodiments, immunotherapy may be active immunotherapy, in which treatment relies on the in vivo stimulation of the endogenous host immune system to react against tumors or infected cells with the administration of immune response-modifying agents (such as polypeptides and polynucleotides disclosed herein).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T cells as discussed above, T lymphocytes (such as CD8+ cytotoxic T lymphocytes and CD4+ T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. In a preferred embodiment, dendritic cells are modified in vitro to present the polypeptide, and these modified APCs are administered to the subject. T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Administration and Dosage

The compositions are administered in any suitable manner, often with pharmaceutically acceptable carriers. Suitable methods of administering cells in the context of the present invention to a subject are available, and, although more than one route can be used to administer a particular cell composition, a particular route can often provide a more immediate and more effective reaction than another route.

The dose administered to a patient, in the context of the present invention, should be sufficient to effect a beneficial therapeutic response in the patient over time, or to inhibit disease progression. Thus, the composition is administered to a subject in an amount sufficient to elicit an effective immune response to the specific antigens and/or to alleviate, reduce, cure or at least partially arrest symptoms and/or complications from the disease. An amount adequate to accomplish this is defined as a "therapeutically effective dose."

Routes and frequency of administration of the therapeutic compositions disclosed herein, as well as dosage, will vary from individual to individual, and may be readily established using standard techniques. In general, the pharmaceutical compositions and vaccines may be administered, by injection (e.g., intracutaneous, intratumoral, intramuscular, intravenous or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. In one embodiment, 2 intradermal injections of the composition are administered 10 days apart.

A suitable dose is an amount of a compound that, when administered as described above, is capable of promoting an anti-tumor immune response, and is at least 10-50% above the basal (i.e., untreated) level. Such response can be monitored, for example, by measuring the anti-tumor antibodies in a patient or by vaccine-dependent generation of cytolytic effector cells capable of killing the patient's tumor cells in vivo. Such vaccines should also be capable of causing an immune response that leads to an improved clinical outcome (e.g., more frequent remissions, complete or partial or longer disease-free survival) in vaccinated patients as compared to nonvaccinated patients. In general, for pharmaceutical compositions and vaccines comprising one or more polypeptides, the amount of each polypeptide present in a dose ranges from about 100 μg to 5 mg per kg of host. Suitable volumes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a tumor protein generally correlate with an improved clinical outcome. Such immune responses may generally be evaluated using standard proliferation, cytotoxicity or cytokine assays, which may be performed using samples obtained from a patient before and after treatment.

EXAMPLES

The following examples are presented to illustrate the present invention and to assist one of ordinary skill in making and using the same. The examples are not intended in any way to otherwise limit the scope of the invention.

Example 1

Identification of Biomarkers for Ovarian Cancer Using Strong Anion-Exchange ProteinChips This example demonstrates three ovarian cancer biomarker protein panels that, when used together, effectively distinguished serum samples from healthy controls and patients with either benign or malignant ovarian neoplasia.

In summary, 184 serum samples from patients with ovarian cancer (n=109), patients with benign tumors (n=19), and healthy donors=56) were analyzed on strong anion-exchange surfaces using surface-enhanced laser desorption/ionization time-of-flight mass spectrometry technology. Univariate and multivariate statistical analyses applied to protein-profiling data obtained from 140 training serum samples identified three biomarker protein panels. The first panel of five candidate protein biomarkers, termed the screening biomarker panel, effectively diagnosed benign and malignant ovarian neoplasia (95.7% sensitivity, 82.6% specificity, 89.2% accuracy, and receiver operating characteristic (ROC) area under the curve of 0.94). The other two panels, consisting of five and four candidate protein biomarkers each, effectively distinguished between benign and malignant ovarian neoplasia and were therefore referred to as validation biomarker panel I (81.5% sensitivity, 94.9% specificity, 88.2% accuracy, and ROC=0.94) and validation biomarker panel II (72.8% sensitivity, 94.9% specificity, 83.9% accuracy, and ROC=0.90). The three ovarian cancer biomarker protein panels correctly diagnosed 41 of the 44 blinded test samples: 21 of 22 malignant ovarian neoplasias (10 of 11 early-stage ovarian cancer (I/II) and 11 of 11 advanced-stage ovarian cancer (III/IV)), 6 of 6 low malignant potential, 5 of the 6 benign tumors, and 9 of 10 normal patient samples.

The following abbreviations are used in this example: CA125, ovarian cancer antigen 125; LMP, low malignant potential; ROC, receiver operating characteristic; SBP, screening biomarker panel; SAX2, strong anion-exchange; SELDI-TOF-MS, surface-enhanced laser desorption/ionization time-of-flight MS; VBP, validation biomarker panel.

Methods

Materials. Serum samples were obtained from healthy individuals (n=56), patients with ovarian cancer (n=109), and patients with benign tumors (n=19) through the Gynecological Oncology Group and Cooperative Human Tissue Network. Serum samples had been collected preoperatively from patients with malignant and benign ovarian tumors. Sample numbers used for profiling (training group) and validation (test group) are listed according to histopathology in Table 1, and the stage and grade of tumors from patients with ovarian cancer are listed in Table 2.

TABLE 1

Sample number used in training and test groups according to histopathology

| Histopathology | Training group | Test group | Total |
| --- | --- | --- | --- |
| Normal | 46 | 10 | 56 |
| Benign | 13 (7S, 6M) | 6 (1S, 4M, 1A) | 19 |
| Adenocarcinoma of LMP | 14 (7S, 7M) | 6 (2S, 3M, 1A) | 20 |
| Adenocarcinoma | 67 (43S, 7M, 7A, 8E, 2C) | 22 (12S, 2M, 2A, 5E, 1C) | 89 |
| Total | 140 | 44 | 184 |

S, serous;
M, mucinous;
A, S or M;
E, endometrioid;
C, clear cell.

TABLE 2

Stage vs. grade of adenocarcinoma samples

| Stage vs. grade | Adenocarcinoma of the ovary | | | | | |
| --- | --- | --- | --- | --- | --- | --- |
| | LMP | Grade 1 | Grade 2 | Grade 3 | Grade 4 | Unknown | Total |
| Stage I | 18 | 10 | 12 | 2 | 2 | 0 | 44 |
| Stage II | 1 | 0 | 7 | 4 | 0 | 0 | 12 |
| Stage III | 1 | 7 | 12 | 11 | 14 | 7 | 52 |
| Stage IV | 0 | 0 | 0 | 0 | 1 | 0 | 1 |
| Total | 20 | 17 | 31 | 17 | 17 | 7 | 109 |

Preparation of Serum Samples for SELDI Analysis. Two different dilutions (1:4 and 1:25) of serum samples were processed on strong anion-exchange (SAX2) chips according to the manufacturer's protocols (Ciphergen Biosystems). Briefly, the array spots were preactivated with binding buffer (1×PBS/0.1% Triton X-100, pH 7.5) at room temperature for 15 min in a humidifying chamber. Each serum sample was first diluted 1:2 or 1:5 with 9 M urea/2% Chaps/50 mM Tris·HCl, pH 9.0, and was further diluted 1:2 or 1:5, respectively, in binding buffer. Three microliters of each diluted sample was spotted onto preactivated SAX2 protein array chips and incubated in a humidity chamber for 30 min at room temperature. The chips were washed twice with binding buffer and once with HPLC $H_2O$, and then air-dried. The chips were then sequentially treated with sinapinic acid (3,5-dimethoxy-4-hydroxycinnamic acid), first with 0.6 µl of a 100% saturated solution followed by 0.8 µl of a 50% saturated solution. The sinapinic acid solution was 50% acetonitrile and 0.5% trifluoroacetic acid. The chips were analyzed with the Ciphergen ProteinChip Reader (model PBSII). Each dilution was analyzed separately to confirm reproducibility in identifying the differentially expressed proteins.

Ciphergen ProteinChip SELDI-TOF-MS Analysis. The arrays were analyzed with the Ciphergen ProteinChip Reader (model PBSII). The mass spectra of proteins were generated by using an average of 65 laser shots at a laser intensity of 230-280 arbitrary units. For data acquisition of low molecular weight proteins, the detection size range was between 2 and 18 kDa, with a maximum size of 25 kDa. The laser was focused at 10 kDa. The detector sensitivity was set at 8, and the laser intensity was set at 230 for the 1:4 and 250 for the 1:25 dilution. For the high molecular weight proteins, the detection size range was between 20 and 150 kDa, with a maximum size of 250 kDa. The laser was focused at 85 kDa. The detector sensitivity was set at 9, and the laser intensity was set at 260 for the 1:4 dilution and 280 for the 1:25 dilution. The mass-to-charge ratio (m/z) of each of the proteins captured on the array surface was determined according to externally calibrated standards (Ciphergen Biosystems, Fremont, Calif.): bovine insulin (5,733.6 Da), human ubiquitin (8,564.8 Da), bovine cytochrome c (12,230.9 Da), bovine superoxide dismutase (15,591.4 Da), bovine β-lactoglobulin A (18,363.3 Da), horseradish peroxidase (43,240 Da), BSA (66,410 Da), and chicken conalbumin (77,490 Da).

Statistical Analysis. The data were analyzed with PROTEINCHIP data analysis software version 3.0 (Ciphergen Biosystems). For each comparison, the raw intensity data were normalized by using the total ion current of all profiles in the groups compared. The peak intensities were normalized to the total ion current of m/z between 3,000 and 25,000 Da for the low molecular weight range and between 4,000 and 250,000 Da for the high molecular weight range. The test group (n=44) was normalized to all 140 training samples before using their intensities against the statistically derived intensity cutoffs. The Biomarker Wizard application (nonparametric calculations; Ciphergen Biosystems) was used to compile all spectra and autodetect quantified mass peaks. Peak labeling was completed by using second-pass peak selection with 0.3% of the mass window, and estimated peaks were added. Sample statistics were performed on groups of profiles (normal vs. benign/cancer and normal/benign vs. cancer). Protein differences (fold changes) were calculated among the various groups. A protein was considered differentially expressed in the ovarian cancer groups if when compared with the normal group, statistically significant differences in its intensity were observed ($P \leq 0.01$) in both the 1:4 and the 1:25 dilution analysis. Using the intensities derived from the 1:25 dilution analysis, univariate comparisons of marker intensity summary statistics of representative markers were performed using statistical analysis software (SAS, Version 8.0, SAS Institute, Cary, N.C.). For each marker, t tests and Wilcoxon rank sum tests were used to compare the mean and median standardized intensities, respectively, between the normal and cancer groups and to determine their corresponding P values (nonparametric for medians). The SAS program was used to determine the "best" intensity cutoff for each marker at either highest accuracy or when sensitivity equals specificity. Receiver operating characteristic (ROC) curves (plot of sensitivity vs. (1-specificity) for each possible cutoff) were generated for proteins with low P values, and the highest individual diagnostic power was calculated by using SAS. Multivariate logistic regression analysis was performed on the biomarkers using SAS. The program was used to analyze various combinations of markers giving predictive scores for each panel tested. This predictive score is a sum of the individually weighted marker intensities.

Results

Identification of Differentially Expressed Ovarian Cancer-Associated Proteins in Serum. Using SELDI-TOF-MS proteomics technology (Ciphergen Biosystems), proteins differentially expressed between serum from healthy individuals (n=46) and serum from patients with ovarian cancer (benign, n=13; low malignant potential (LMP), n=14; and malignant, n=67) were identified. A representative pseudo-gel view of specific candidate ovarian cancer tumor markers and a spectral overlay of candidate markers from healthy vs. diseased individuals are shown in FIGS. 1A and 1B. Statistical analysis on potential biomarkers with the lowest P values ($\leq 0.01$). The P values were generated with nonparametric tests from both the BIOMARKER WIZARD application (Ciphergen Biosystems) and the SAS program. Sensitivity, specificity, overall accuracy, and ROC area values were computed for each biomarker using the SAS program.

Neoplasia Biomarkers and Malignant Neoplasia Biomarkers. Proteins that are differentially expressed in healthy individuals vs. patients with any ovarian tumor, including benign or malignant, were considered first. Under the conditions tested, 10 biomarkers were identified (4.1 kDa, 4.4 kDa, 7.7 kDa, 12.9 kDa, 15.1 kDa, 15.9 kDa, 18.9 kDa, 23.0 kDa, 30.1 kDa, and 53.5 kDa) and classified as "neoplasia biomarkers" (markers best at identifying benign and malignant samples). All markers, except marker 12.9 kDa, showed increased expression in patients with ovarian cancer. At highest accuracy, the individual markers in the neoplasia biomarkers group had ROC area values ranging from 0.711 to 0.833, sensitivities from 60.6% to 84.0%, specificities from 52.2% to 89.1%, and accuracies from 67.1% to 78.5%.

Proteins that are differentially expressed in healthy individuals and individuals with benign tumors vs. patients with malignant ovarian tumors were examined next. Under the conditions tested, 13 proteins (3.1 kDa, 4.5 kDa, 5.1 kDa, 7.8 kDa, 8.2 kDa, 13.9 kDa. 16.9 kDa, 18.6 kDa, 21.0 kDa, 28.0 kDa. 79.0 kDa, 93.0 kDa, and 106.7 kDa) were identified and grouped as "malignant neoplasia biomarkers" (markers best at identifying malignant samples). Markers 3.1 kDa, 4.5 kDa, 5.1 kDa, 7.8 kDa, 8.2 kDa, 16.9 kDa, and 18.6 kDa showed increased expression in patients with ovarian cancer, whereas markers 13.9 kDa, 21.0 kDa, 28.0 kDa, 79.0 kDa, 93.0 kDa, and 106.7 kDa showed decreased expression in patients with ovarian cancer. The individual proteins in the malignant biomarkers group had values for ROC area ranging from 0.617 to 0.851, sensitivities from 48.1% to 81.5%, specificities from 66.1% to 88.1%, and accuracies from 61.3% to 79.3%.

Figure 2:
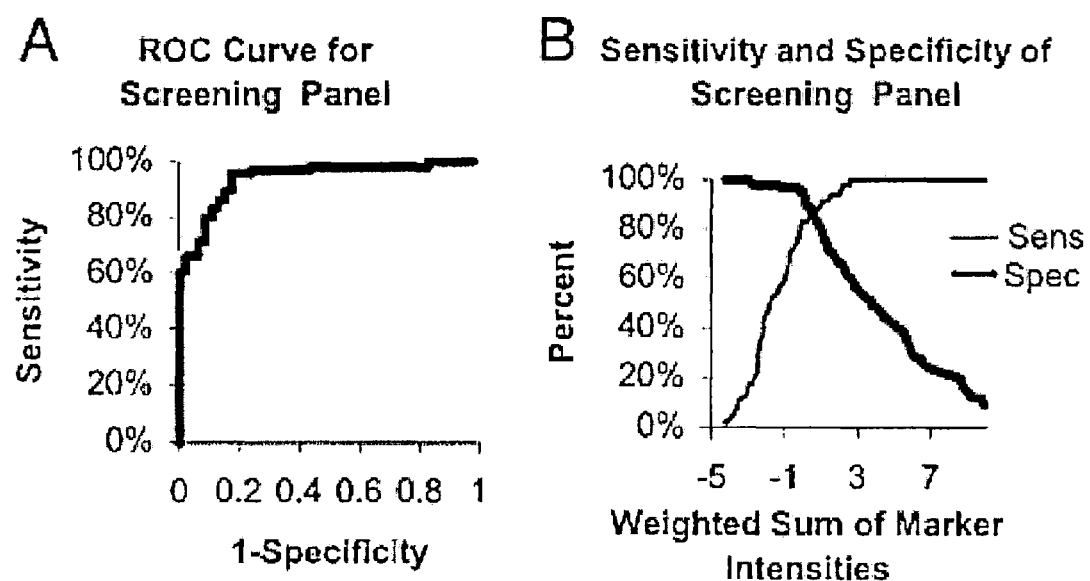
FIGS. 2A-2B show ROC curves and plot of sensitivity and specificity for the ovarian cancer screening panel. ROC curve analysis was based on 140 patients to compare the diagnostic performance of five neoplasia biomarkers making up the screening panel (4.4 kDa, 15.9 kDa, 18.9 kDa, 23.0 kDa, and 30.1 kDa), which were identified by the SAS multivariate analysis program. The area under the ROC curve is 0.94 (2A), and the weighted sum of the marker intensities (score/index) is plotted as a function of sensitivity and specificity (2B).
Figure 3:
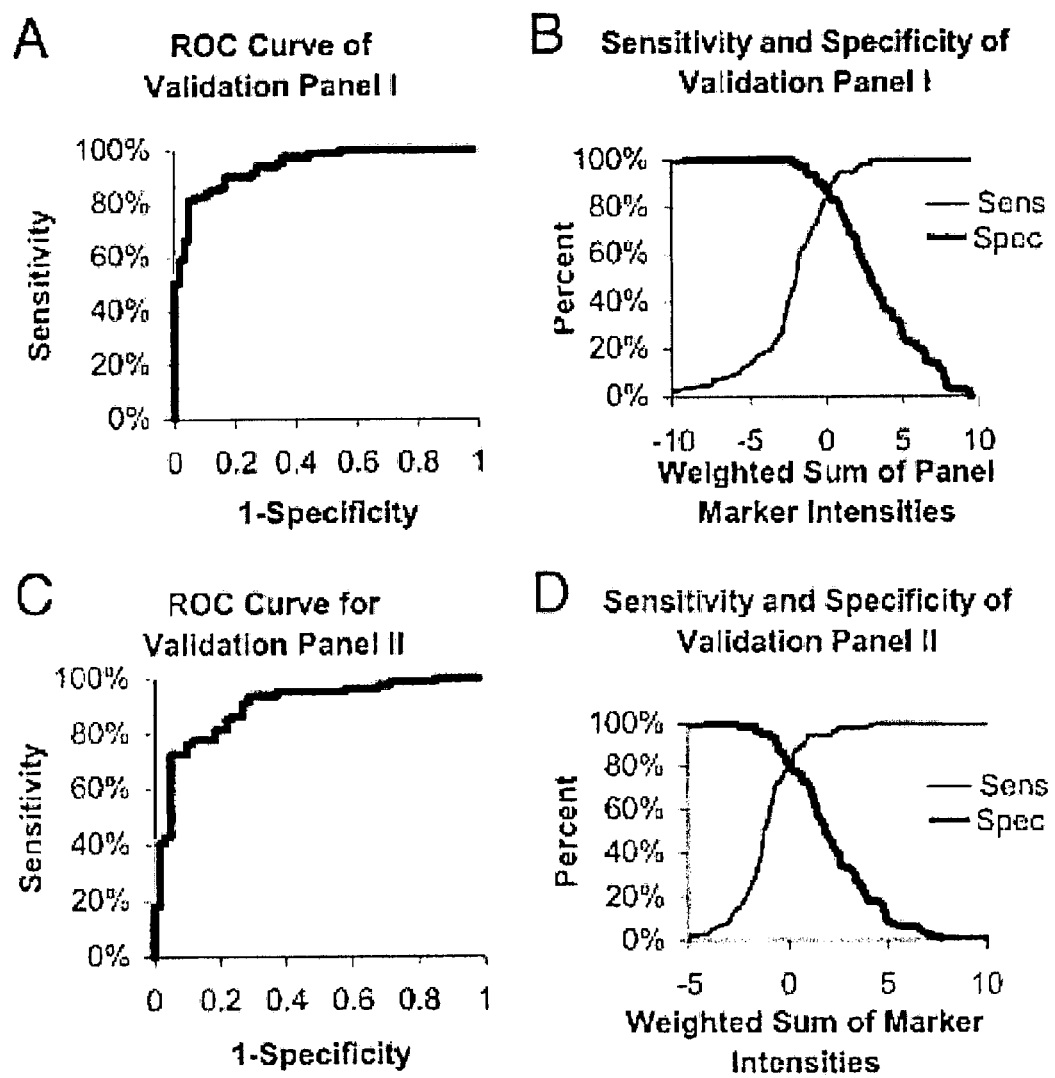
FIGS. 3A-3D show ROC curves and plot of sensitivity and specificity for the ovarian cancer validation panels I and II. Five malignant neoplasia biomarkers making up the validation panel I (3.1 kDa, 13.9 kDa, 21.0 kDa, 79.0 kDa, and 106.7 kDa) and four markers representing the validation panel II (5.1 kDa, 16.9 kDa, 28.0 kDa, and 93.0 kDa) were identified by the SAS multivariate analysis program. The areas under the ROC curves are 0.94 (3A) and 0.90 (3C). The weighted sum of the marker intensities (score/index) is plotted as a function of sensitivity and specificity (3B and 3D).

Biomarker Panels. Multivariate analysis was performed on both the neoplasia and malignant neoplasia groups, separately, to identify panels of biomarkers that will diagnose ovarian neoplasm (benign or malignant) or distinguish between benign and malignant ovarian tumors. The SAS program, through a process of statistical logistic backward elimination to avoid "overfitting" bias, produced panels with the least redundant markers. Thus, these markers were excluded from the panel. Multivariate analysis of the 10 candidate ovarian neoplasia biomarkers resulted in an ovarian cancer screening biomarker panel (SBP) of five markers (4.4 kDa, 15.9 kDa, 18.9 kDa, 23.0 kDa, and 30.1 kDa) with a collective ROC area (0.94; FIG. 2A) higher than the best individual ovarian neoplasia diagnostic biomarker (0.83; 15.1 kDa). The sensitivity, specificity, and overall accuracy for the SBP were 95.7%, 82.6%, and 89.2%, respectively (Table 3 and FIG. 2B). Similarly, multivariate analyses of the 13 malignant neoplasia biomarkers yielded two independent panels: validation biomarker panel (VBP) I of five markers (3.1 kDa, 13.9 kDa, 21.0 kDa, 79.0 kDa, and 106.7 kDa) and VBP II of four markers (5.1 kDa, 16.9 kDa, 28.0 kDa, and 93.0 kDa) with ROC area values (0.94 and 0.90; Table 3 and FIGS. 3A and 3C) higher than the best individual malignant ovarian neoplasia diagnostic biomarker (0.85; 79.0 kDa). The sensitivity, specificity, and overall accuracy values for the VBPs were 81.5%, 94.9%, and 88.2% for panel I and 72.8%, 94.9%, and 83.9% for panel II, when maximizing overall accuracy (Table 3 and FIGS. 3B and 3D).

TABLE 3

Statistical summary of biomarker panels

| Ovarian cancer panels | Sensitivity, % | | Specificity, % | | Accuracy,* % | | ROC Area |
|---|---|---|---|---|---|---|---|
| | A | B | A | B | A | B | |
| Screening biomarker panel | 86.2 | 95.7 | 87.0 | 82.6 | 86.6 | 89.2 | 0.94 |
| Validation biomarker panel I | 85.2 | 81.5 | 84.7 | 94.9 | 85.0 | 88.2 | 0.94 |
| Validation biomarker panel II | 81.5 | 72.8 | 81.4 | 94.9 | 81.4 | 83.9 | 0.90 |

A values are represented when sensitivity equals specificity. B values are represented at their highest accuracy.
*Accuracy is 0.5 sensitivity + 0.5 specificity Screening and Validation of Test Samples. The SBP and the VBPs were tested on 44 blinded test samples (10 normal, 6 benign, 6 LMP, and 22 invasive ovarian cancers, and 11 early-stage (I/II) and 11 advanced-stage (III/IV) carcinomas). For the ovarian cancer SBP, the test sensitivity (number benign and cancer correctly labeled positive/number true positive) at highest accuracy was 91.2%, the test specificity (number normal correctly labeled negative/number true negative) was 80%, and test accuracy was 85.6%. For early-stage (I/II), the SBP using the highest accuracy cutoff resulted in a sensitivity of 100% (identified 11 of 11), advanced-stage (III/IV) sensitivity of 100% (identified 11 of 11), benign tumor sensitivity of 50% (3 of 6), and a nontumor specificity of 80% (identified 8 of 10 nondiseased). For the ovarian cancer VBP I, the overall test sensitivity, specificity, and accuracy were 71.4%, 100%, and 85.7%, respectively, and resulted in test sensitivity for earlystage (I/II) of 54.5% (identified 6 of 11), and for advanced-stage (III/IV) of 72.7% (identified 8 of 11), benign tumor specificity of 100% (identified 6 of 6), and nontumor specificity of 100% (identified 10 of 10). Finally, for the ovarian cancer VBP II, the overall test sensitivity, specificity, and accuracy were 89.3%, 56.3%, and 72.8%, respectively, and resulted in test sensitivity for early-stage (I/II) of 90.9% (identified 10 of 11) and 81.8% for advanced-stage (III/IV; identified 9 of 11), with benign tumor specificity of 50% (identified 3 of 6) and nontumor specificity of 60% (identified 6 of 10). Predictions made with all three panels together, by using their score thresholds at highest accuracy, correctly diagnosed 41 of 44 test samples: 21 of 22 malignant carcinomas (10 of 11 early-stage (I/II), 11 of 11 advanced-stage (III/IV)), 6 of 6 LMP, 5 of the 6 benign tumors, and 9 of 10 normal patient samples.

Example 2

Characterization of Ovarian Cancer Serum Biomarkers for Early Detection

This example demonstrates the identification, characterization, and validation of the proteins that represent the SELDI-TOF-MS peaks from the ovarian cancer biomarker panels. Mass spectrometry and other analytical methods were employed to identify proteins of interest in human serum. The Example describes the identity of proteins that represent the m/z peaks 12.9, 13.8, 15.1, 15.9, 28 and 78.9 kDa in the ovarian cancer biomarker panels. Using micro-liquid chromatography-tandem mass spectrometry, the following m/z peaks were identified as: transthyretin (TTR): 12.9 kDa and 13.9 kDa, hemoglobin, both alpha-hemoglobin (alpha-Hb): 15.1 kDa, and beta-hemoglobin (beta-Hb): 15.9 kDa, apolipoprotein AI (ApoAI): 28 kDa and transferrin (TF): 78.9 kDa. Western and ELISA techniques (independent of SELDI) confirmed the differential expression of TTR, Hb and TF in a group of ovarian cancer serum samples. Multivariate analyses improved the detection of early stage ovarian tumors (low mallignant potential and malignant) as compared to cancer antigen CA125 alone. Multivariate analysis with only the mucinous subtype of early stage ovarian tumors showed the marker to greatly improve the detection of disease as compared to CA125 alone.

This Example uses the following abbreviations: CA125, ovarian cancer antigen 125; Hb, hemoglobin; LMP, low malignant potential; µLC-MSMS, micro-liquid chromatography-tandem mass spectrometry; ROC, receiver operating characteristic; SAS, statistical analysis software; SAX2, strong anion exchange; SELDI-TOF-MS, Surface-Enhanced Laser Desorption/Ionization Time-of-Flight Mass Spectrometry; TF, transferrin; TTR, tranthyretin.

Materials

Serum samples were obtained through the Gynecological Oncology Group and Cooperative Human Tissue Network and had been collected preoperatively. Purified protein preparations of transthyretin (TTR), hemoglobin (Hb), transferrin (TF) and apolipoprotein AI (ApoAI), were purchased from Sigma-Aldrich (St. Louis, Mo.).

Serum Protein Fractionation

Serum (30 ul) was desalted on P-6 Micro Bio-Spin chromatography columns (Bio-Rad, Hercules Calif.) and dealbuminized using Affi-Gel Blue Gel (Bio-Rad, Hercules, Calif.) in micro columns according to the manufacturer's protocol. Serum was fractionated using anion exchange spin columns (Ciphergen, Fremont, Calif.), by eluting with a series of buffers decreasing in pH (20 mM sodium phosphate, pH 7.0 and 6.3; 50 mM sodium acetate, pH 5.0 and 4.0; 100 mM sodium citrate, pH 2.5 and 2.3 with or without 1M sodium chloride). Protein fractions were analyzed on strong anion exchange (SAX2) chips using a SELDI-TOF-MS PSII as reported previously.

Serum Protein Purification, Passive Elution and Confimation by SELDI-TOF-MS

Fractions confirmed by SELDI-TOF-MS to contain a significant majority of the 13.9 kDa peak using either an NP20 or Au chip according to the manufacturer's protocol (Ciphergen, Fremont Calif.) were pooled and dried by centrifugal evaporation. Fractions containing the 15.9 and 79 kDa proteins were further purified on SDS-PAGE. The gels were then stained with Simply Blue Safestain (Invitrogen, Carlsbad, Calif.), bands with molecular weights corresponding to the markers were excised, gel slices were cut in half, and half of the gel slice was passively eluted according to Le Bihan et al. (17). Briefly, the gel was dehydrated with acetonitrile for ≥10 min, dried in a heat block for 10 min at 42° C. and rehydrated in 50% formic acid/25% acetonitrile/ 15% isopropyl alcohol. Tubes were placed in a sonicator bath for 30 min followed by vortexing for 1 h. A fraction of the eluate was applied onto an NP20 or Au chip and profiles were compared to regions of serum profiles corresponding to markers 15.9 and 79 kDa. The 28 kDa protein was purified from dealbuminized serum using PHM-L Liposorb (Calbiochem, San Diego Calif.), followed by SDS-PAGE. Protein from half of the gel slide was passively eluted and confirmed by SELDI-TOF-MS.

Tryptic Digestion and μLC-MSMS

Concentrated pooled anion exchange fractions containing the 13.9 kDa marker were reduced (10 mM DTT in 50 mM ammonium bicarbonate; 30 min, 24° C.), alkylated (55 mM iodoacetamide in 50 mM ammonium bicarbonate; 20 mM, 24° C.), and treated with trypsin (Promega; 6 ng/μl in 50 mM ammonium bicarbonate; 3 h. 37° C.). After confirming that the passively eluted proteins from half of the SDS-PAGE gel slice corresponded to the 15.9, 28 and 79 kDa markers, the remaining half was used for in gel tryptic digest. Briefly, the gel slices were destained in 200 mM ammonium bicarbonate/40% acetonitrile, washed with a 1:1 mixture of 100 mM ammonium bicarbonate: acetonitrile for 10 min and dehydrated with acetonitrile 10 min. After vacuum drying 5 min, the gel slices were reduced with 10 mM DTT in 50 mM ammonium bicarbonate for 60 min at 60° C. After cooling, gel slices were incubated for 45 min at 45° C. with 50 mM iodoacetic acid in 50 mM ammonium bicarbonate. After washing and dehydrating the gel slices with 100 mM ammonium bicarbonate and acetonitrile for 10 min, they were vacuum dried and tryptic digestion performed with 50 mM ammonium bicarbonate containing 10 ng/ml trypsin in an ice bath for 45 min. Additional 50 mM ammonium bicarbonate was added and digestion was continued overnight at 37° C. Peptides were recovered by saturating the gel slices with HPLC grade water and extracted with 50% acetonitrile containing 1% trifloroacetic acid three times for 10 min each. Extracts were dried in a cold speedvac for 1 hr. Dried samples were analyzed by micro-liquid chromatography-tandem mass spectrometry (μLC-MSMS) as described previously (18) and the data was used to search human databases using Sonar ms/Ms™ (Genomic Solutions, Ann Arbor Mich.) and TurboSEQUEST™ (Thermo Electron Corp., San Jose Calif.). Briefly, samples were analyzed by μLC-MSMS with data-dependent acquisition (LCQ-DECA, ThermoFinnigan, San Jose, Calif.) after dissolution in 5 μl of 70% acetic acid (v/v). A reverse-phase column (200 μm×10 cm, PLRP/S 5 μm, 300 Å; Michrom Biosciences, San Jose, Calif.) was equilibrated with 95% A, 5% B (A, 0.1% formic acid in water; B, 0.1% formic acid in acetonitrile) and a linear gradient was initiated ramping to 60% A, 40% B after 50 min and 20% 0.1% A, 80% B after 65 min. Column eluent was directed to a coated glass electrospray emitter (TaperTip, TT150-5050-CE-5, New Objective) at 3.3 kV for ionization without nebulizer gas. The mass spectrometer was operated in "triple-play" mode with a survey scan (400-1500 m/z), data-dependent zoom scan, and MSMS.

Western Blot Analysis

Total serum protein was determined by Bradford assay using BSA as the standard (Sigma-Aldrich, St. Louis Mo.) and equal protein amounts (0.1-30 μg) or volume (1 μl) was loaded onto SDS-PAGE gels. Western analyses were performed as described previously (19). Rabbit anti-TTR antibody was purchased from DAKO (Carpinteria, Calif.).

Goat anti-Hb was obtained from Bethyl Laboratories Inc. (Montgomery, Tex.), goat anti-ApoAI from Biodesign international (Saco, Me.), and goat anti-seroTF was from Abeam Inc. (Cambridge, Mass.). Secondary antibodies, anti-goat IgG and anti-rabbit IgG (both conjugated to HRP), were used at a 1:4000 dilution.

Immunoprecipitation

Serum (~250 μg) was pre-cleared in immunoprecipitation buffer (1% Triton X 100/0.025% sodium azide/0.1M NaCl/ 0.05M Tris-HCl, pH7.5/5 mM EDTA and protease inhibitors) with 6% v/v A/G Plus agarose beads (Sigma-Aldrich, St. Louis Mo.) for 3 h at 4° C. with tumbling. Beads were removed by centrifugation for 30 s at 13.2K rpm, antibodies were added to the supernatant and rotated at 4° C. overnight. The antibody/antigen complexes were precipitated by adding 6% v/v A/G Plus agarose beads for 3.5 h, at 4° C. Beads were removed from depleted serum by centrifugation for 30 s at 13.2K rpm. Post pre-cleared and depleted samples were analyzed on SELDI-TOF-MS with SAX2 chips as previously reported.

ELISA

For TTR and ApoAI, optimized dilutions of pure proteins and serum samples were coated onto 96-well Immobilon plates overnight at 4° C. in coating buffer (0.1M carbonate buffer, pH 9.6; 1:10,000 for TTR; 1:10,000 for ApoAI). After washing, plates were blocked with 0.05% Tween 20/0.25% BSA/1×PBS at RT for 1 h. Primary TTR antibody was used at a 1:10,000 dilution and secondary antibody (rabbit-HRP) was used at a 1:5,000 dilution. Primary ApoAI antibody was used at a 1:10,000 dilution and secondary antibody (goat-HRP) was used at a 1:5,000 dilution. Detection was performed with TMB (KPL, Gaithersburg, Md.) and stopped with 0.5M sulfuric acid. Hb and TF ELISA kits were purchased from Bethyl Laboratories Inc. (Montgomery, Tex.) and used according to the manufacturer's protocols with optimized serum and antibody concentrations. Hb capture antibody was used at a 1:100 dilution, HRP detection antibody at a 1:10,000 dilution, while serum was diluted 1:10,000. TF capture antibody was used at a 1:100 dilution, HRP detection antibody at a 1:150,000 dilution and the serum was diluted 1:50,000. The CA125 ELISA kit was purchased from BioCheck (Burlingame, Calif.) and used according to the manufacturer's protocol. Plates were read in a Kinetic microplate reader (Molecular Devices, Sunnyvale Calif.) at 450 nm and analysis was performed using the SoftMax Pro v4.3 LS software (Molecular Devices, Sunnyvale Calif.).

Statistical Analysis

SELDI-TOF-MS data was analyzed with Ciphergen's ProteinChip data analysis software version 3.0 (Ciphergen Biosystems, Fremont Calif.). SELDI-TOF-MS and ELISA marker intensities were analyzed using statistical analysis software (SAS, Version 8.0, SAS Institute, Cary N.C.). The Mann-Whitney non-parametric two-tailed t-test with 95% confidence interval was used to determine p-values.

Results

Figure 4:
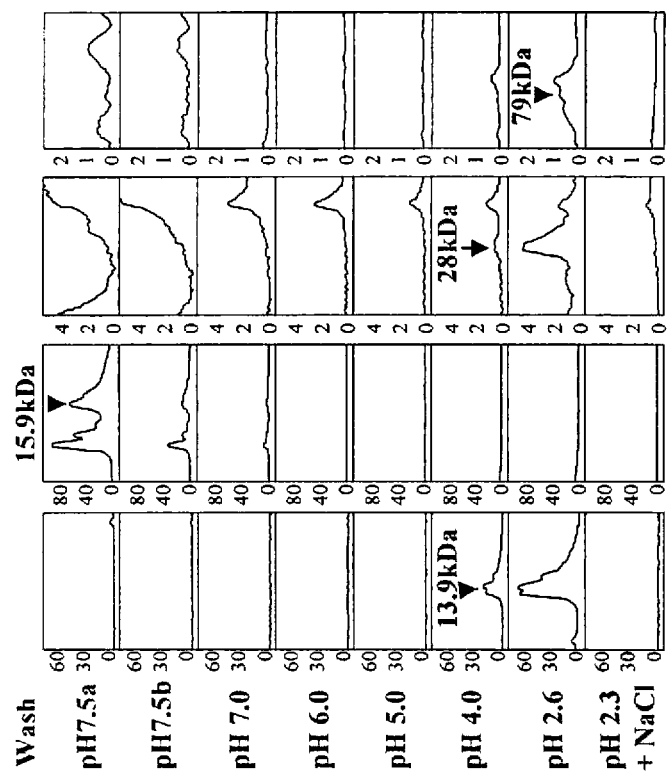
FIG. 4 illustrates determination of the pI for ovarian cancer markers by anion exchange fractionation. SAX2 SELDI-TOF-MS profiles of anion exchange fractions depict differentially expressed ovarian cancer markers. After desalting and dealbuminization, the serum proteins were eluted from Ciphergen anion exchange columns with a series of buffers decreasing in pH and were analyzed on SAX2 ProteinChips as mentioned in Methods and Materials.

Identification of potential candidate proteins using size, pI and TagIdent. From the pool of markers reported previously (16), we chose five biomarker proteins (12.9, 13.9, 15.9, 28.0, and 79 kDa) for the current studies; 12.9, 13.9, 28.0, and 79 decreased in patients with ovarian cancer whereas 15.9 increased in patients with ovarian cancer. We performed an online TagIdent (protein database) search using the size determined from SELDI-TOF-MS analysis and the corresponding pI as determined by anion exchange fractionation (FIG. 4). The m/z values used for the searches were 12785, 13797, 15850, 27977, and 78715, corresponding to markers, 12.9, 13.9, 15.9, 28 and 79 respectively. Using search criteria allowing for a 0.5% size error and ±2 pI range, we identified TTR, beta-Hb, and ApoAI, as potential candidate proteins for m/z peaks 13.9, 15.9, and 28 respectively. The m/z peak 79 and its corresponding pI did not result in any candidate proteins in our analysis, however: recently a similar 79 kDa SELDI peak from a separate ovarian cancer profiling study was identified as TF.

Figure 5:
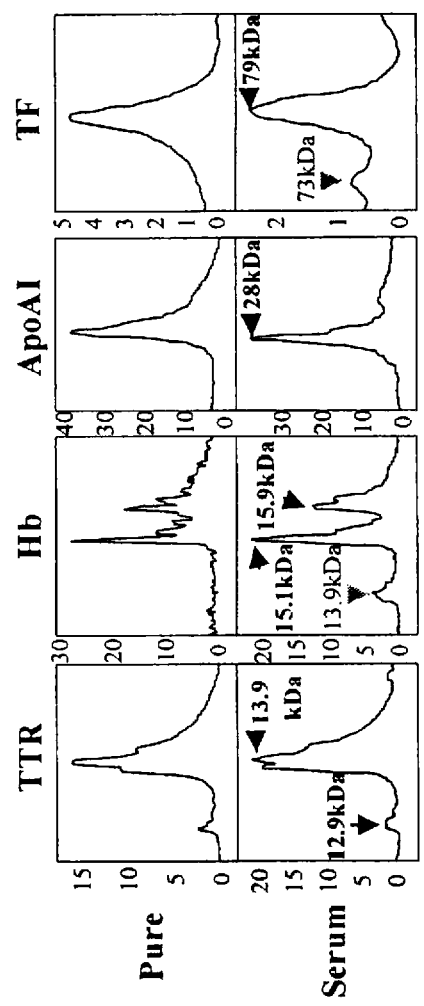
FIG. 5 shows that the SELDI profiles of purified TTR, Hb, ApoAI and sero-TF match with the 12.9, 13.9, 15.1, 15.9, 28 and 79 m/z peaks from the human serum. Pure proteins (0.1-1 μg) of TTR, Hb, ApoAI and TF, diluted 1:5 in 9M Urea/2% CHAPS/50 mM Tris-HCl, pH9.0 and further diluted 1:5 in 1×PBS/0.1% Triton X-100, pH7.5, were analyzed on SAX2 chips and compared with SELDI-TOF-MS peaks obtained for 12.9, 13.9, 15.1, 15.9, 28 and 79 m/z peaks from the human serum. Marker sizes in "bold" with black arrows identify the ovarian cancer serum markers aligning with pure proteins and distinguish them from other identified serum proteins (indicated by gray arrows).

The SELDI-TOF-MS profiles of purified TTR, Hb, ApoAI and sero-TF matched with the 12.9, 13.9, 15.1, 15.9, 28 and 79 m/z peaks from the human serum. We purchased purified (from human serum) preparations of the candidate proteins and compared their SELDI-TOF-MS profiles to those generated from serum samples for 12.9, 13.9, 15.9, 28 and 79 (FIG. 5). Pure TTR protein resulted in peaks with an m/z similar to that obtained for both 12.9 and 13.9 kDa serum markers. Pure Hb gave a peak of m/z similar to the 15.9 kDa serum marker, likely corresponding to the beta chain, while a second peak from the pure Hb matched with one of our original (16) non-panel serum markers (15.1 kDa) likely correlating with the alpha subunit of Hb. Pure ApoAI protein resulted in a peak with an m/z similar to that obtained for the 28 kDa serum marker, while the peak from pure sero-TF aligned with the 79 kDa marker peak.

Fractionation and tryptic peptide fragmentation and analysis by tandem mass spectrometry confirmed the identities of biomarker proteins as TTR, Hb, ApoAI and TF. To further confirm the identities of the five biomarkers, the peaks corresponding to the respective sizes were partially purified from serum following dealbuminization and anion exchange chromatography (FIG. 4). The partially purified proteins were subjected to tryptic digestion followed by µLC-MSMS analysis and the resulting fragments were searched against human protein databases (Sonar and SEQUEST). The results confirmed the 13.9 kDa protein as TTR, beta-Hb as the 15.9 kDa protein, ApoAI as the 28 kDa protein and TF as the 79 kDa protein. We also confirmed the non-panel 15.1 kDa marker as alpha-Hb. Due to limitations in obtaining sufficient quantities we did not perform pLC-MSMS analysis on the 12.9 kDa marker. However, a similar 12.9 kDa SELDI-TOF-MS peak has been recently reported to be a fragment of TTR by purification and mass spectrometry analysis. Moreover, we have also observed that pure TTR protein contains two peaks with m/z ratios similar to that obtained for 12.9 and 13.9 kDa serum markers (FIG. 5) suggesting that the 12.9 kDa peak is indeed a TTR fragment.

Figure 6:
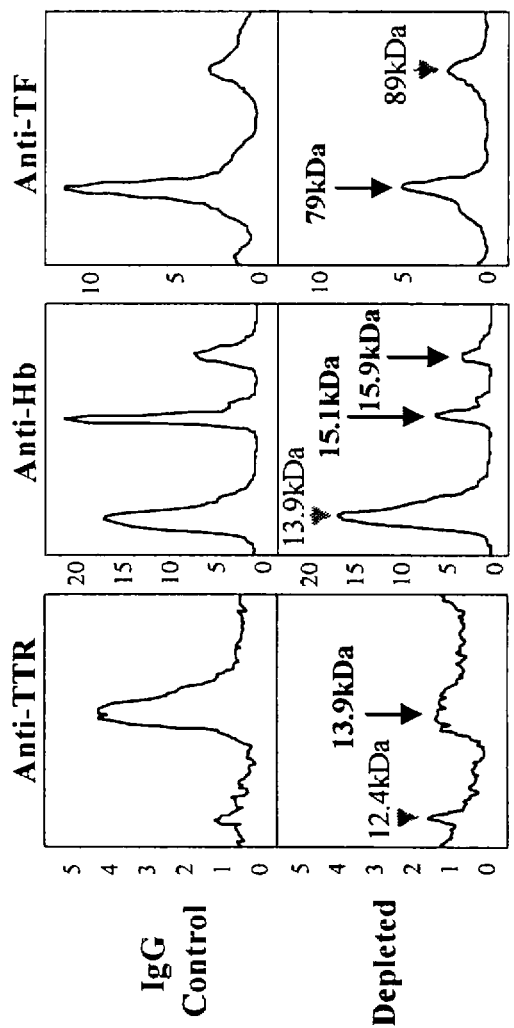
FIG. 6 shows that immunodepletion studies validate TTR, Hb and TF as the proteins corresponding to the 13.9, 15.1, 15.9 and 79 kDa peaks. Pre-cleared serum was immunoprecipitated with 5-30 μg of antibody and A/G agarose beads. Post pre-cleared and depleted samples were diluted with an equal volume of Chaps/Urea buffer (9M Urea/2% Chaps/50 mM Tris-HCl pH 9.0), followed by 0.5 volume of binding buffer (1×PBS/0.1% Triton-X 100, pH 7.5), and analyzed on SAX2 chips. SAX2 SELDI-TOF-MS protein profiles show the successful depletion of specific peaks after immunoprecipitation with TTR, Hb, and TF antibody. Marker sizes in "bold" with black arrows identify depleted ovarian cancer serum markers and distinguish them from other identified serum proteins that were not depleted (indicated by gray arrows).

Immunodepletion studies further validated TTR, alpha-Hb, beta-Hb and TF as the proteins corresponding to the 13.9, 15.1, 15.9 and 79 kDa peaks. We next performed immunoprecipitation studies on pre-cleared normal serum to ensure that the SELDI-TOFMS peaks of the five markers correspond to the proteins identified by the methods described above. Immunoprecipitation of TTR and TF from pre-cleared normal serum resulted in depletion of the 13.9 kDa and 79 kDa protein (FIG. 6). Immunoprecipitation of Hb from pre-cleared serum derived from an ovarian cancer patient, resulted in depletion of the 15.1 and 15.9 kDa proteins (FIG. 6).

Westerns confirmed TTR, Hb, and TF to be differentially expressed in serum from ovarian cancer patients. Using specific antibodies, we further confirmed the differential expression of TTR, Hb, and TF in serum samples from normal individuals, and patients with early stage (I/II) or late stage (III/IV) ovarian cancer by Western blotting. Membranes probed with anti-TTR or anti-sero-TF showed a decrease in protein levels (FIG. 7), while anti-Hb antibody showed an increase in expression between normal, early and late stage ovarian cancer (FIG. 7). No significant differential expression was observed for ApoAI on Western blots.

Figure 8:
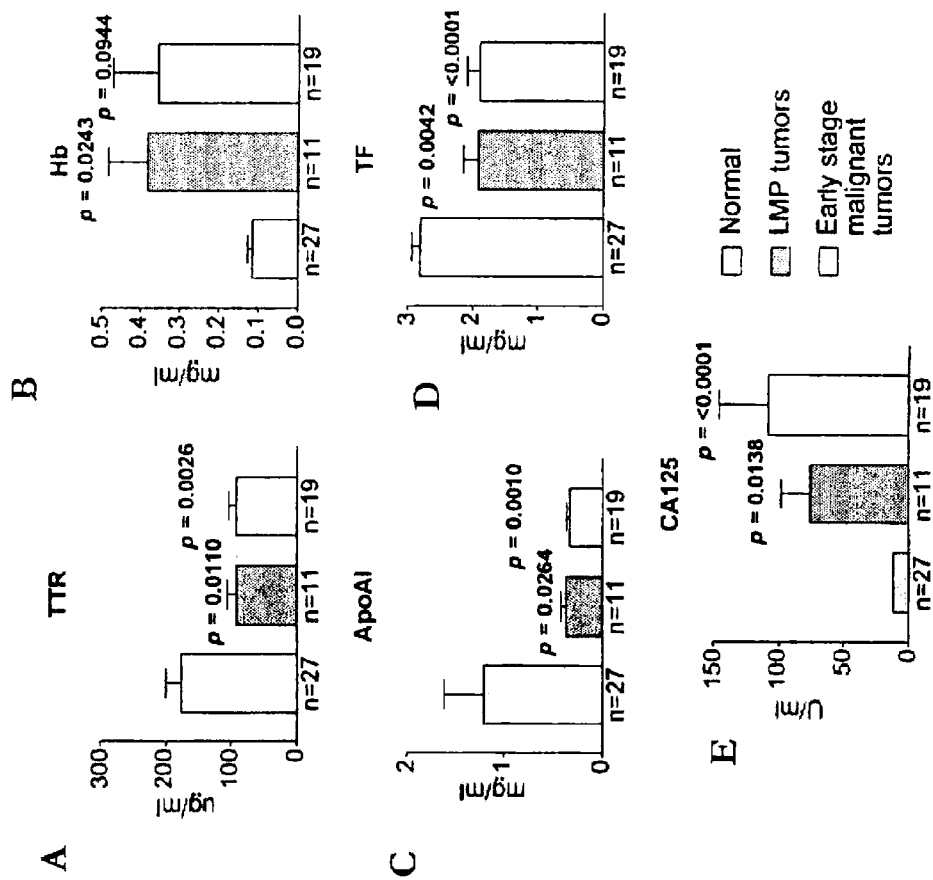
FIGS. 8A-8E show that TTR (8A), Hb (8B), ApoAI (8C), TF (8D) and CA125 (8E) levels distinguish normal individuals from individuals with early stage ovarian tumors as determined by ELISA. Serum samples from 27 normal individuals, 11 individuals with ovarian LMP and 19 individuals with early stage (I/II) ovarian cancer, were analyzed by ELISA for TTR, Hb, ApoAI, TF and CA125 as described under Materials and Methods. Plates were read at 450 nm and analyzed using SoftMax Pro v4.3 LS software (Molecular Devices, Sunnyvale, Calif.).

ELISA experiments validated TTR, Hb, ApoAI and TF as biomarkers for ovarian tumors. Differential expression of TTR, Hb, ApoAI and TF was further validated in ELISA experiments performed with 27 normal samples, 11 ovarian low malignant potential tumor (LMP) samples and 19 early stage malignant ovarian tumor samples (FIG. 8A-8E). For the early stage malignant ovarian tumors, the TTR concentration was approximately 175±25 µg/ml in the normal serum, while it was only 91±12 in the early stage ovarian cancers (FIG. 8A). Interestingly, Swiss-protein database indicates normal levels of TTR to be between 100-400 µg/ml. Hb (FIG. 8B) indicated a significant difference between normal serum (0.11±0.01 mg/ml) and early stage serum (0.35±0.12). The ApoAI concentration was approximately 1.21±0.41 mg/ml in the normal serum, while it was only 0.33±0.02 mg/ml in the early stage ovarian cancers (FIG. 8C). Swiss-protein database indicates normal levels of ApoAI to be 0.9-2.1 mg/ml. In the malignant samples tested, the concentration for TF (FIG. 8D) was 2.82±0.12 mg/ml for normal and 1.88±0.19 mg/ml for early stage. Swiss-protein database indicates normal levels of TF to be 2-4 mg/ml. All antibodies, except for TTR, had been tested to work in ELISA assays.

Statistical analysis of ELISA data from normal and early stage ovarian tumors identify TTR, Hb, ApoAI and TF as markers for early detection of ovarian tumors. The differential expression of our proteins between normal samples and LMP tumors was determined to be statistically significant for all markers (FIG. 8A-8E). The differential expression between normal samples and early stage tumor samples was significant for all individual markers, except Hb (FIG. 8B). We performed multivariate regression analysis with the ELISA data generated from the LMP and the malignant tumors and compared sensitivity, specificity and ROC values from our characterized markers, together, to CA125 alone or in combination with our markers (Table 4a, b). Table 4a and b indicate sensitivity and specificity, when they are given equal importance, and ROC values of multivariate regression analysis of our markers for LMP tumors, early stage malignant tumors and LMP and malignant tumors as generated by SAS. Results show that our markers, combined with CA125, improve sensitivity, specificity and ROC values for all histological groups (serous papillary, mucinous, endometrioid, and clear cell; Table 4a) as well as for the mucinous subgroup (Table 4b).

TABLE 4a

Multivariate analysis of marker ELISA values for detection of early stage ovarian tumors in all histological groups.

| Normal n = 27 | Markers | Sensitivity & Specificity* (%) | ROC Area |
|---|---|---|---|
| LMP (n = 11) | CA125 | ~64% | 0.758 |
|  | TTR, Hb, ApoAI, TF | ~82% | 0.953 |
|  | TTR, Hb, ApoAI, TF, CA125 | ~82% | 0.949 |
| Malignant (n = 19) | CA125 | ~85% | 0.875 |
|  | TTR, Hb, ApoAI, TF | ~85% | 0.920 |
|  | TTR, Hb, ApoAI, TF, CA125 | ~89% | 0.971 |
| LMP & Malignant (n = 30) | CA125 | ~78% | 0.833 |
|  | TTR, Hb, ApoAI, TF | ~86% | 0.933 |
|  | TTR, Hb, ApoAI, TF, CA125 | ~86% | 0.959 |

*Values are represented when threshold cutoffs are set where sensitivity and specificity are given equal importance TABLE 4b Multivariate analysis of marker ELISA values for detection of early stage ovarian tumors of the mucinous histological subgroup

| Normal n = 27 | Markers | Sensitivity & Specificity* (%) | ROC Area |
|---|---|---|---|
| LMP (n = 6) | CA125 | ~51% | 0.562 |
|  | TTR, Hb, ApoAI, TF | ~81% | 0.926 |
|  | TTR, Hb, ApoAI, TF, CA125 | ~84% | 0.932 |
| Malignant (n = 3) | CA125 | ~67% | 0.728 |
|  | TTR, Hb, ApoAI, TF | ~100% | 1.000 |
|  | TTR, Hb, ApoAI, TF, CA125 | ~100% | 1.000 |
| LMP & Malignant (n = 9) | CA125 | ~56% | 0.613 |
|  | TTR, Hb, ApoAI, TF | ~87% | 0.959 |
|  | TTR, Hb, ApoAI, TF, CA125 | ~87% | 0.955 |

*Values are represented when threshold cutoffs are set where sensitivity and specificity are given equal importance Discussion We reported the identification of several ovarian cancer biomarkers generated using Ciphergen's ProteinChip technology. When used as panels, these markers resulted in improved sensitivity and specificity for the detection of early stage ovarian cancer. In this example, we report the identification of proteins that represent the previously reported biomarkers with m/z ratios 12.9, 13.9, 15.9, 28 and 79 kDa as a TTR fragment, TTR, beta-Hb, ApoAI and TF, respectively. We also identified a non-panel marker, 15.1 kDa, as alpha-Hb. We have shown that together, TTR, Hb, ApoAI, TF and CA125 can improve ovarian tumor (all histological subgroups) detection sensitivity by 8% when compared to CA125 alone (threshold cutoff where sensitivity and specificity are equally important). More interestingly, TTR, Hb, ApoAI, TF, and CA125, together improved sensitivity of detecting mucinous tumors by 31% over CA125 alone.

The detection sensitivities for our markers when tested against a pool of serum samples that contained all histological groups of ovarian cancer are similar to those reported by other investigators. Rai et al. identified and purified transferrin, immunoglobulin heavy chain and a fragment of the haptoglobin precursor protein as candidate biomarkers of ovarian cancer using SELDI-TOF-MS technology with nickel-coated immobilized metal affinity capture type 3 arrays (IMAC3). Statistical analysis of these data demonstrated that the diagnostic index combining two of the biomarkers (the 60 and 79 kd peaks), and CA125, improved sensitivity by more than 10% over that of CA125 alone. More recently, Zhang et al. (2004) identified three biomarkers for the detection of early stage ovarian cancer from serum proteomics analysis using multiple chips. They identified a 28 kDa band to be ApoAI (down-regulated), a 12.8 kDa band to be a truncated form of TTR (down-regulated), and a 3.2 kDa band as a cleavage fragment of inter-alpha-trypsin inhibitor heavy chain H4 (up-regulated). Statistical analysis demonstrated that combining the three biomarkers (3.2, 12.8 and 28 kDa peaks) and CA125 level, improved sensitivity by 9% over that of CA125 level alone. However, it should be noted that our results from multivariate analyses were performed using values derived entirely from ELISA, a potentially more clinically relevant assay, rather than SELDI-TOF-MS intensity values.

One of the markers identified in the present study, ApoAI, is the major apolipoprotein of high density lipoprotein and is an abundant plasma protein. Recently, Zhang et al. reported that ApoAI is differentially expressed in patients with ovarian cancer and is a good marker for early stage ovarian cancer. ApoAI levels have been found to also decrease during tangier disease and arteriosclerosis. Another marker identified in our study, TTR, is a secreted protein with a molecular mass of 13.8 kDa that functions as a binding protein to transport thyroxine and retinal (vitamin A). TTR is decreased in patients with ovarian carcinoma, advanced cervical and endometrial carcinomas. Mahlck and Grankvist, showed that TTR concentrations are lower in women with carcinoma of the ovary than in postmenopausal controls and the levels correlate inversely to tumor volume, suggesting prognostic significance. TTR is also known to decrease during severe liver disease, malnutrition and acute inflammation.

When analyzed as a marker by itself, Hb turned out to be a significant biomarker for the detection of ovarian tumors (LMP), however, the marker was not significantly differentially expressed in early stage malignant tumors with non-parametric analysis (although is was significant with parametric analysis). We were initially concerned with this finding since mechanical handling and/or sample preparation can potentially result in RBC lysis and Hb release. Therefore, to reduce the analysis of Hb released as an artifact, we omitted samples that were obviously red from our analyses and in subsequent careful repetitions of these experiments we confirmed that Hb is not an artifact but rather a specific and significant serum biomarker of ovarian cancer. Alpha- and beta-Hb chains are primarily involved in oxygen transport, forming a heterotetramer of two alpha chains and two beta chains in adult hemoglobin A. The alpha- and beta-Hb are proteins with molecular masses 15.1 kDa and 15.8 kDa, respectively and have not been identified as markers for ovarian cancer previously. It has been reported that biochemical modifications of the erythrocyte membranes in women with ovarian cancer may increase susceptibility to hemolysis of red blood cells. Hb has been reported to also increase in polycythemia vera.

Transferrin is an iron binding transport protein, which can bind two atoms of ferric iron in association with the binding of an anion, usually bicarbonate. Transferrin is responsible for the transport of iron from sites of absorption and heme degradation to those of storage and utilization. The TF gene encodes a 77-80 kDa protein and has been reported to decrease in the serum of patients with ovarian cancer. TF also decreases during inflammation, nephrosis and haemochromatosis.

Recently, there has been strong criticism that SELDI-based analyses mostly identify highly abundant and acute phase proteins. Of the five markers we identified and characterized in this study, only two markers fall in the class of acute phase proteins (TTR and TF). Moreover, preliminary analyses show that most of the remaining nine markers from our original panels are not abundant serum proteins.

Statistical analysis of the ELISA data for LMP and malignant tumors showed all markers to be significant (p≤0.05) for LMP tumors, and all markers (with the exception of Hb [p=0.092]), were significant for early stage malignant tumors (FIG. 8A-E). Multivariate analysis of the combined markers improved detection of LMP tumors over CA125 by 18%, and 30% for the mucinous subtype, while the combined markers, with CA125, did not significantly improve the ROC for all histological groups or the mucinous subgroup (0.953 to 0.949, 0.926 to 0.932, respectively). For the malignant tumors, the statistical analysis resulted in an increase of ROC (0.875 to 0.920) when comparing CA125 alone to our markers, while the addition of CA125 to our combined markers increased the ROC from 0.920 to 0.971. The high sensitivity, specificity and ROC values for the mucinous malignant tumors may be due to the low number of samples analyzed (n=3).

LMP (n=6) and malignant ovarian tumors (n=3) showed that our combined markers improve detection of early stage tumors over CA125 by 8%, and improved detection of the mucinous subgroup by 31%. The addition of CA125 to our combined markers increased the ROC for early stage detection of ovarian tumors for all histological groups (0.933 to 0.959), but not for the mucinous group (0.959 to 0.955). Multivariate analysis of early stage mucinous tumors (LMP and malignant) showed our markers to greatly improve the detection of disease (ROC 0.959) as compared to CA125 only (ROC 0.613). The addition of CA125 to the multivariate analysis of our markers did not seem to further improve the detection of mucinous tumors (ROC 0.955).

Although our markers are differentially expressed in other diseases, the difference in directionality (increasing or decreasing) and the ability to combine multiple markers allows us to specifically detect early stage ovarian cancer. In preliminary data, we have found our markers to be ovarian cancer specific when comparing differential expression of our markers in other cancers such as breast, colon, and epithelial, and to other diseases such as atherosclerosis. We plan to analyze our markers in additional cancers and diseases, as well as analyze additional samples. Thus, our characterized markers, even if they are not released directly by the tumor, could be used in combination with other markers, such as CA125, to improve the sensitivity and specificity of early stage ovarian cancer.

In conclusion, we have characterized five m/z SELDI ovarian cancer biomarker peaks and confirmed their differential expression in serum using Western and ELISA assays. We have identified and characterized TTR, Hb, ApoAI and TF as proteins that are differentially expressed in early stage ovarian tumors. Together, these markers have improved detection of early stage ovarian tumors relative to CA125 alone. These markers should facilitate the development of additional clinical assays, such as ELISAs, to improve early detection of ovarian cancer.

Example 3

Identification of Additional Ovarian Cancer Serum Biomarkers

This example demonstrates the identification of additional biomarkers from serum samples that exhibit sensitivity and specificity in detecting ovarian neoplasia. These biomarkers were identified using SELDI as described above. The following table lists the protein identity, m/z ratios (in Daltons, "Marker"), cut point, sensitivity ("Sens"), specificity ("Spec"), accuracy ("Acc") of each biomarker. Subsequent columns indicate the mean level observed for each biomarker in the screening (normal and neoplasm) and validation (nonmalignant and malignant) panels. N=140.

TABLE 5

|  |  |  |  |  |  | Mean Level of Biomarker | | | |
|---|---|---|---|---|---|---|---|---|---|
|  |  |  |  |  |  | Screening | | Validation | |
| Protein | Marker | Cut Point | Sens | Spec | Acc | Normal | Neoplasm | Non-Malignant | Malignant |
|  | M1953 | 1.18 | 0.70 | 0.63 | 0.67 | 1.57 | 4.25 | 2.95 | 3.67 |
|  | M2065 | 1.70 | 0.63 | 0.70 | 0.66 | 1.73 | 3.23 | 2.63 | 2.81 |
|  | M2216 | 0.87 | 0.65 | 0.63 | 0.64 | 1.04 | 2.60 | 1.81 | 2.30 |
|  | M2928 | 1.35 | 0.55 | 0.83 | 0.69 | 0.79 | 2.06 | 1.38 | 1.84 |
|  | M2937 | 1.79 | 0.69 | 0.72 | 0.70 | 1.81 | 3.35 | 2.14 | 3.36 |
|  | M3143 | 1.59 | 0.65 | 0.65 | 0.65 | 1.64 | 2.59 | 2.02 | 2.47 |
|  | M3423 | 0.48 | 0.57 | 0.74 | 0.66 | 0.57 | 1.54 | 0.71 | 1.59 |
|  | M3427 | 0.58 | 0.66 | 0.67 | 0.67 | 0.63 | 1.66 | 1.04 | 1.52 |
|  | M4144 | 4.26 | 0.74 | 0.63 | 0.69 | 4.46 | 6.79 | 5.25 | 6.59 |
|  | M4375 | 0.98 | 0.76 | 0.59 | 0.67 | 0.94 | 1.54 | 0.97 | 1.61 |
|  | M4456 | 2.01 | 0.60 | 0.87 | 0.73 | 1.36 | 3.05 | 1.54 | 3.19 |
|  | M4629 | 3.48 | 0.35 | 0.93 | 0.64 | 2.22 | 3.20 | 2.42 | 3.21 |
|  | M5064 | 1.21 | 0.73 | 0.70 | 0.71 | 1.16 | 2.11 | 1.18 | 2.24 |
|  | M6884 | 7.77 | 0.67 | 0.93 | 0.80 | 10.46 | 6.87 | 10.12 | 6.54 |
|  | M6931 | 10.08 | 0.70 | 0.80 | 0.75 | 12.29 | 8.31 | 12.05 | 7.85 |
|  | M7550 | 0.96 | 0.86 | 0.65 | 0.76 | 1.09 | 3.13 | 1.70 | 3.01 |
|  | M7657 | 1.19 | 0.57 | 0.89 | 0.73 | 0.75 | 1.45 | 0.92 | 1.44 |
|  | M7756 | 1.12 | 0.48 | 0.91 | 0.70 | 0.65 | 1.25 | 0.68 | 1.32 |
|  | M8117 | 2.16 | 0.76 | 0.76 | 0.76 | 1.82 | 2.61 | 1.94 | 2.65 |
|  | M10874 | 0.35 | 0.85 | 0.43 | 0.64 | 0.42 | 0.50 | 0.41 | 0.52 |
|  | M12785 | 1.17 | 0.61 | 0.80 | 0.71 | 1.46 | 1.12 | 1.33 | 1.16 |
| TTR | M13797 | 22.73 | 0.74 | 0.91 | 0.83 | 27.77 | 18.72 | 26.53 | 18.17 |
| HBA | M15074 | 1.38 | 0.81 | 0.76 | 0.78 | 1.50 | 4.47 | 2.23 | 4.42 |
| HBB | M15850 | 1.29 | 0.67 | 0.83 | 0.75 | 1.08 | 4.09 | 1.83 | 4.02 |
|  | M16850 | 0.24 | 0.59 | 0.91 | 0.75 | 0.12 | 0.33 | 0.15 | 0.35 |
|  | M18559 | 0.29 | 0.60 | 0.72 | 0.66 | 0.27 | 0.45 | 0.25 | 0.49 |
|  | M18912 | 0.07 | 0.63 | 0.76 | 0.69 | 0.05 | 0.13 | 0.06 | 0.13 |
|  | M18980 | 0.08 | 0.49 | 0.78 | 0.64 | 0.05 | 0.10 | 0.05 | 0.10 |

TABLE 5-continued

| | | | | | | Mean Level of Biomarker | | |
| | | | | | | | | Validation |
| | | Cut | | | | Screening | Non- | |
| Protein | Marker | Point | Sens | Spec | Acc | Normal | Neoplasm | Malignant | Malignant |
|---|---|---|---|---|---|---|---|---|---|
| | M19186 | 0.10 | 0.33 | 1.00 | 0.66 | 0.03 | 0.07 | 0.03 | 0.08 |
| | M20989 | 0.66 | 0.66 | 0.85 | 0.75 | 0.77 | 0.63 | 0.74 | 0.63 |
| | M22959 | 1.15 | 0.70 | 0.85 | 0.77 | 1.06 | 1.39 | 1.08 | 1.43 |
| | M27595 | 0.50 | 0.73 | 0.89 | 0.81 | 0.91 | 0.41 | 0.83 | 0.39 |
| APOA1 | M27977 | 0.54 | 0.48 | 0.85 | 0.66 | 1.52 | 0.79 | 1.47 | 0.71 |
| | M29190 | 0.81 | 0.38 | 0.89 | 0.64 | 0.69 | 0.76 | 0.72 | 0.75 |
| | M29512 | 0.68 | 0.68 | 0.67 | 0.68 | 0.61 | 0.76 | 0.65 | 0.75 |
| | M30103 | 0.56 | 0.84 | 0.52 | 0.68 | 0.55 | 0.75 | 0.57 | 0.76 |
| | M33217 | 12.80 | 0.49 | 0.83 | 0.66 | 11.61 | 12.84 | 11.92 | 12.81 |
| | M36296 | 0.55 | 0.59 | 0.85 | 0.72 | 0.42 | 0.76 | 0.42 | 0.82 |
| | M40067 | 0.30 | 0.60 | 0.93 | 0.77 | 0.47 | 0.29 | 0.47 | 0.27 |
| | M42401 | 0.36 | 0.60 | 0.70 | 0.65 | 0.34 | 0.40 | 0.33 | 0.42 |
| α1-AT | M53110 | 0.11 | 0.43 | 0.98 | 0.70 | 0.04 | 0.17 | 0.05 | 0.18 |
| | M53531 | 0.04 | 0.62 | 0.80 | 0.71 | 0.03 | 0.12 | 0.03 | 0.13 |
| | M54605 | 0.18 | 0.76 | 0.61 | 0.68 | 0.20 | 0.16 | 0.16 | 0.18 |
| TF | M78715 | 1.05 | 0.78 | 0.85 | 0.81 | 1.46 | 0.78 | 1.38 | 0.73 |
| | M79909 | 1.28 | 0.63 | 0.87 | 0.75 | 1.71 | 1.13 | 1.69 | 1.05 |
| | M83689 | 0.04 | 0.63 | 0.72 | 0.67 | 0.03 | 0.10 | 0.05 | 0.10 |
| | M84133 | 0.02 | 0.69 | 0.74 | 0.72 | 0.02 | 0.05 | 0.03 | 0.06 |
| | M90834 | 0.18 | 0.52 | 0.80 | 0.66 | 0.22 | 0.18 | 0.21 | 0.17 |
| | M91878 | 0.19 | 0.48 | 0.89 | 0.69 | 0.25 | 0.19 | 0.25 | 0.19 |
| | M92935 | 0.24 | 0.59 | 0.89 | 0.74 | 0.29 | 0.21 | 0.29 | 0.20 |
| | M105778 | 0.06 | 0.65 | 0.80 | 0.73 | 0.09 | 0.05 | 0.09 | 0.04 |
| IgG | M106624 | 0.09 | 0.56 | 0.91 | 0.74 | 0.12 | 0.08 | 0.12 | 0.08 |

Example 4

Serum Biomarkers for Detection of Early- and Late-Stage Endometrial Cancer

This example demonstrates the efficacy of 3 of the above-described ovarian cancer serum biomarkers (apolipoprotein-1 [ApoA-I], prealbumin [TTR], transferrin [TF]) in the detection of endometrioid and papillary serous adenocarcinoma of the endometrium. ApoA-I, TTR, and TF levels were measured in serum samples that were obtained from 433 individuals that included 90 women with normal endometrium, 210 women with early-stage endometrial cancer, and 133 women with late-stage endometrial cancer. Multivariate regression models were constructed to evaluate the usefulness of the biomarkers in the detection of endometrial cancer. ApoA-I, TTR, and TF distinguished normal samples from early-stage endometrial cancer with a sensitivity of 71% (specificity, 88%) and normal samples from late stage endometrial cancer with a sensitivity of 82% (specificity. 86%). The biomarker panel that consists of ApoA-I, TTR, and TF thus provides a useful clinical tool for the detection of endometrial cancer.

Materials and Methods

Serum samples were obtained through the Gynecological Oncology Group (GOG) and Cooperative Human Tissue Network. Samples were collected preoperatively according to the standard GOG protocol (GOG-199 protocol). The levels of each individual protein marker (CA125, ApoA-I, TTR, TF) were measured on all serum samples, as described above. The immunoassay analyzer (Immulite 1000; Siemens Healthcare Diagnostics, Deerfield, Ill.) was used to measure CA125 level with chemiluminescence technology, and the chemistry analyzer (Hitachi 912; Roche Diagnostics, Basel, Switzerland) was used to measure ApoA-I, TTR, and TF levels based on immunoturbimetry technology, as previously described in Su et al., 2007, Biomarkers Insights 2:369-75. The reagents were purchased from Diagnostics Product Corporation and Roche.

The 433 serum samples that were used in this study included samples from 90 women with normal uteri (N), 210 women with early-stage endometrial cancer (ESEC), and 133 women with late-stage endometrial cancer (LSEC). ESEC was defined as stages I-II. LSEC was defined as stages III-IV. All patients were appropriately staged according to the GOG Surgical Manual. The age and pathologic distribution of the samples are provided in Table 6.

TABLE 6

Clinical characteristics and age distribution of 433 study samples

| | | | | | Pathologic condition | | |
| Diagnostic group | n | Age | | | Endometrioid adenocarcinoma | Clear cell | Serous carcinoma |
| | | Mean | SD | Median | | | |
|---|---|---|---|---|---|---|---|
| Normal | 90 | 44.6 | 11.7 | 45 | | | |
| Early stage | 210 | 63.7 | 12.1 | 63 | 162 | 10 | 38 |
| Late stage | 133 | 66.7 | 13.0 | 67 | 55 | 13 | 65 |

Each cancer stage (eg, ESEC and LSEC) and its corresponding histologic subcategory (eg, endometrioid, clear cell, and serous adenocarcinoma; together or individually) were compared with the normal group to identify an association to the set of markers of interest (ApoA-I, TTR, TF, and CA125), with the use of multiple logistic regression (MLRM). Based on the MLRM, we computed predicted probabilities of patients with malignant disease. We report sensitivity and specificity for each diagnostic model by identifying the cutoff point of the predicted probability that yields the maximum sum of sensitivity and sensitivity. To validate our models, we used 10-fold cross validation with the largest difference in the area under the curve (AUC) being within 3% of the original model.

Descriptive statistics of the levels of each individual marker (ApoA-I, TTR, TF, and CA-125) were presented as means (SD) to compare marker levels across all sample categories. MLRMs were built to predict normal vs ESEC and normal vs LSEC. All tests were 2-sided and a probability value of <0.05 was considered statistically significant. All tests were performed with the SAS statistical package (version 9.1; SAS Institute Inc, Cary, N.C.).

patients with endometriod adenocarcinoma, serum CA125 levels distinguished normal samples from ESEC with a sensitivity of only 12% and normal from LSEC with a sensitivity of only 38% (Table 7). In serum samples from patients with serous, CA125 was able to distinguish normal samples from early-stage serous carcinoma with a sensitivity of only 11% and normal from late stage serous carcinoma with a sensitivity of only 49% (Table 7).

TABLE 7

Statistical analysis of cancer antigen 125

| Cancer group | All histologic subtypes | | | Endometrioid adenocarcinoma | | | Serous carcinoma | | |
|---|---|---|---|---|---|---|---|---|---|
| | Sensitivity | Specificity | Area under the curve | Sensitivity | Specificity | Area under the curve | Sensitivity | Specificity | Area under the curve |
| Normal vs early stage | 0.13 | 0.99 | 0.56 | 0.12 | 0.99 | 0.56 | 0.11 | 0.99 | 0.55 |
| Normal vs late stage | 0.41 | 0.99 | 0.70 | 0.38 | 0.99 | 0.69 | 0.49 | 0.99 | 0.74 |

Sensitivity and specificity were calculated based on the results from the receiver operating curve that was constructed with logistic regression at the point at which the sum of the 2 values was maximal.

MLRMs were constructed with the use of the values for ApoA-I, TF, and TTR (CA125 excluded: Table 8). Collectively, ApoA-I, TTR, and TF distinguished (1) normal samples from samples that represented all histopathologic subtypes of ESEC (sensitivity, 71%; specificity, 88%; AUC, 0.86), and (2) normal samples from samples with LSEC (sensitivity, 82%; specificity, 86%; AUC, 0.88). More strikingly, the sensitivity in distinguishing normal vs serous ESEC, with the use of ApoA-I, TF, and TTR (CA125 excluded), was 82% (specificity, 78%; AUC, 0.86; Table 8). When MLRMs were constructed with ApoA-I, TF, and TTR, including CA125, the sensitivity and specificity did not improve in distinguishing normal samples from either ESEC or LSEC (data not shown).

TABLE 8

Statistical analysis of 3 markers (apolipoprotein-1, prealbumin, transferrin)

| Cancer group | All histologic subtypes | | | Endometrioid adenocarcinoma | | | Serous carcinoma | | |
|---|---|---|---|---|---|---|---|---|---|
| | Sensitivity | Specificity | Area under the curve | Sensitivity | Specificity | Area under the curve | Sensitivity | Specificity | Area under the curve |
| Normal vs early stage | 0.71 | 0.88 | 0.86 | 0.70 | 0.89 | 0.86 | 0.82 | 0.78 | 0.86 |
| Normal vs late stage | 0.82 | 0.86 | 0.88 | 0.67 | 0.89 | 0.84 | 0.89 | 0.82 | 0.92 |

Sensitivity and specificity were calculated based on the results from the receiver operating curve that was constructed with logistic regression at the point at which the sum of the 2 values was maximal.

Results

The serum levels of each of the 4 markers (CA125, ApoA-I, TTR, and TF) are significantly different in both patient samples for ESEC and LSEC, when compared with normal serum samples (FIGS. 9A-D).

Serum CA125 levels alone correctly detected only 24% of all the endometrial samples that were tested. The sensitivity of CA125 was only 13% in distinguishing ESEC from normal subjects and only 41% in distinguishing LSEC from normal subjects (Table 7). Moreover, in serum samples from Comment Over the past 2 decades, despite minimal increases in new cases, the number of deaths per year because of endometrial cancer has been increasing.[1] In the 1980s, approximately 3000 estimated deaths could be attributed to endometrial cancer. In the 1990s, this number rose to 5000 per year and in 2006 to 7000.[17] The increase in mortality rates in women with endometrial cancer is related to an increased rate of advanced-stage cancers and high-risk histologic subtypes.[3] From 1988-2001, the proportion of late-stage cancer at diagnosis rose from 14.2-18% and deaths from advanced-stage cases rose from 52.1-68.8%.[3]

At the present time, there are no reliable clinical serum markers for the detection of endometrial cancer. Although CA125 is currently the best clinical marker for women with late-stage ovarian cancer, few studies have identified CA125 to be a useful marker in the early detection of endometrial cancer.[7], [8] and [9] In fact, only 10-20% of patients with ESEC and only 25% of patients with asymptomatic recurrent disease have elevated serum CA125 levels.[18] and [19] Other serum tumor markers have been studied for their potential use, both individually and in combination, to form a panel of proteins in patients with endometrial cancer, including cancer antigen 15-3 (CA15-3), 19-9 (CA19-9), 72-4 (CA72-4), carcinoembryonic antigen (CEA), tumor marker OVX1 and macrophage colony-stimulating factor (M-CSF)[20], [21], [22], [23] and [24] with limited success.

As described in the preceding examples, we validated the use of 3 novel serum biomarkers for the detection of early stage ovarian cancer[16] that included ApoA-I, TTR, and TF.[10], [11], [14], [15] and [16] We reported that these 3 serum proteins, when applied in combination, effectively detected early-stage ovarian cancers with high sensitivity (86%) in a population of ovarian cancer samples similar in histologic condition to those studied in the present example for endometrial cancer and serous and endometrioid adenocarcinoma. With the addition of CA125 to our 3 biomarkers, the sensitivity for the detection of early-stage ovarian cancer improved by only 10% (96%). However, this still represented a large improvement (46%) over the sensitivity that had been reported when CA125 was used alone (50-60%).[25] and [26]

In the present study, we established the sensitivity measurements that are associated with serum CA125 levels in patients with endometrioid and serous adenocarcinoma of the endometrium. CA125 currently is not used clinically for the screening of endometrial cancer. Not surprisingly, our data demonstrated that CA125 was a relatively poor marker for distinguishing normal from either ESEC or LSEC for either histologic subtype (11-12% and 38-46%, respectively; Table 7); these data corroborate the poor diagnostic value of serum CA125 levels for the early detection of patients with endometrial cancer that was reported previously.[23], [27] and [28]

More importantly, we examined whether our 3 markers (ApoA-I, TTR, and TF) could improve on the CA125 levels in our patient samples with endometrial cancer. The sensitivity that was associated with our markers for the detection of ESEC (71%) and LSEC (82%) represented a marked improvement over CA125 (58% and 41%, respectively; Table 7 and Table 8). However, the sensitivity of our markers in the detection of early-stage ovarian cancer was higher (86%).[10], [11] and [16]

Few studies report novel serum biomarkers for the detection of endometrial cancer. Moore et al[28] reported that human epididymis protein 4 and soluble mesothelin-related peptides were associated with low sensitivity in the detection of early-stage I and late-stage II-IV endometrial cancers (44.8% and 59.4%, respectively).

This is the first report of the use of serum levels of ApoA-I, TTR, and TF for the detection of endometrial cancer. Our findings suggest that these 3 markers may be clinically useful in the detection of early-stage disease, when hormonal or surgical treatment modalities can be used to the cure the disease and before the presence of clinical symptoms or signs. In addition, these biomarkers could be used for prognostic purposes and monitoring patients who undergo treatment and surveying posttreatment for recurrent disease.

REFERENCES

1. Endometrial cancer. In: T. L. Callahan and A. B. Caughey, Editors, *Blueprints obstetrics and gynecology* (5th ed.), Lippincott Williams & Wilkins, Philadelphia. Pa. (2008), pp. 310-316.
2. Y. Sonoda and R. Barakat, *Best Pract Res an Obstet Gynaecol* 20 (2006), pp. 363-377.
3. S. Ueda, et al., *Am J Obstet Gynecol* 198 (2008), pp. 218.e1-218.e6.
4. H. Jhang, et al., *Am J Obstet Gynecol* 188 (2003), pp. 1195-1197.
5. R. C. Bast Jr, et al., *N Engl J Med* 309 (1983), pp. 883-887.
6. P. Kenemans, et al., *Clin Chem* 39 (1993), pp. 2509-2513.
7. D. J. Dotters, *Am J Obstet Gynecol* 182 (2000), pp. 1328-1334.
8. N. P. Koper, et al., *Anticancer Res* 18 (1998), pp. 1897-1902.
9. S. S. Lo, et al., *Tumour Biol* 18 (1997), pp. 241-249.
10. V. Nossov, et al., *Am J Obstet Gynecol* 199 (2008), pp. 215-223.
11. V. Nossov, et al., *Am J Obstet Gynecol* 200 (2009), pp. e1-e3.
12. J. D. Wulfkuhle, et al., *Nat Rev Cancer* 3 (2003), p. 267.
13. L. R. Zhu, et al., *Int J Gynecol Cancer* 16 (2006), pp. 1374-1378.
14. F. Su, et al. *Biomarkers Insights* 2 (2007), pp. 369-375.
15. K. R. Kozak, et al., *Proc Natl Acad Sci USA* 100 (2003), pp. 12343-12348.
16. K. R. Kozak, et al., *Proteomics* 5 (2005), pp. 4589-4596.
17. A. Jemal, et al., Cancer statistics, 2006, *CA Cancer Clin* 56 (2006), pp. 106-130.
18. J. M. Nilodd, et al., *Am J Obstet Gynecol* 148 (1984), pp. 1057-1058.
19. J. M. Duk, et al., *Am J Obstet Gynecol* 155 (1986). pp. 1097-1102.
20. P. L. Cherchi, et al., *Eur Gynaecol Oncol* 20 (1999), pp. 315-317.
21. N. Takeshima, et al., *Gynecol Oncol* 54 (1994), pp. 321-326.
22. H. Hareyama, et al., *J Clin Pathol* 49 (1996), pp. 967-970.
23. E. P. Beck, et al., *Gynecol Oncol* 65 (1997), pp. 291-296.
24. S. S. Lo, et al., *Cancer Detect Prev* 23 (1999), pp. 397-400.
25. I. J. Jacobs and U. Menon, *Mol Cell Proteomics* 3 (2004), pp. 355-366.
26. J. L. Wilder, et al., *Gynecol Oncol* 89 (2003), pp. 233-235.
27. G. Scambia, et al., *Gynecol Oncol* 54 (1994), pp. 292-297.
28. R. G. Moore, et al., *Gynecol Oncol* 110 (2008), pp. 196-201.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of treating endometrial cancer in a subject comprising:
   (a) measuring binding of antibodies in a serum sample obtained from the subject, wherein the antibodies specifically bind three biomarkers consisting of transthyretin (TTR), apolipoprotein AI (ApoAI) and transferrin (TF) in the serum sample;
   (b) administering radiotherapy or chemotherapeutic drugs for endometrial cancer to the subject when a decrease is found in the measured three biomarkers of in the serum sample compared to the measurement of the three biomarkers in the normal sample.

2. The method of claim 1, wherein the decrease in the measured three biomarkers is a decrease of at least 5% compared to the normal sample.

3. The method of claim 1, wherein the decrease in the measured three biomarkers of cancer is a decrease of at least 10% compared to the normal sample.

4. The method of claim 1, wherein the measuring comprises immunoturbimetry.

5. The method of claim 1, wherein the measuring further comprises measuring CA-125 in a serum sample of the subject and comparing the measured CA-125 to a measurement of CA-125 in a normal sample, wherein an increase in the measured CA-125 of the serum sample compared to the normal sample.

6. The method of claim 1, wherein the endometrial cancer comprises endometrioid carcinoma, clear cell carcinoma or serous carcinoma.

7. The method of claim 1, wherein the measuring distinguishes normal samples from early-stage endometrial cancer with a sensitivity of 71%, and/or distinguishes normal samples from late stage endometrial cancer with a sensitivity of 82%.

8. The method of claim 1, wherein the measuring distinguishes normal samples from early-stage endometrial cancer with a specificity of 88%, and/or distinguishes normal samples from late stage endometrial cancer with a specificity of 86%.

9. A method of analyzing a serum sample obtained from a subject comprising:
   (a) contacting the serum sample obtained from a subject suspected of having endometrial cancer with antibodies that specifically bind three biomarkers consisting of transthyretin (TTR), apolipoprotein AI (ApoAI) and transferrin (TF); and
   (b) measuring binding of the antibodies to TTR, ApoAI and TF to measure the three biomarkers in the sample.

10. The method of claim 9, wherein the analyzing further comprises measuring CA-125 in a serum sample of the subject.

11. The method of claim 9, wherein the measuring comprises enzyme-linked immunosorbent assay.

12. The method of claim 9, wherein the measuring comprises enzyme-linked immunoturbimetry.

* * * * *

UNITED STATES PATENT AND TRADEMARK OFFICE
CERTIFICATE OF CORRECTION

PATENT NO. : 9,488,655 B2
APPLICATION NO. : 12/860293
DATED : November 8, 2016
INVENTOR(S) : Farias-Eisner et al.

Page 1 of 1

It is certified that error appears in the above-identified patent and that said Letters Patent is hereby corrected as shown below:

In the Claims

In Column 47, Line 11, delete "of".

Signed and Sealed this
Thirteenth Day of February, 2018

Andrei Iancu
*Director of the United States Patent and Trademark Office*